United States Patent
Clary et al.

(10) Patent No.: US 7,125,869 B2
(45) Date of Patent: Oct. 24, 2006

(54) POLYCYCLIC COMPOUNDS WHICH MODULATE PPARγ TYPE RECEPTORS AND COSMETIC/PHARMACEUTICAL COMPOSITIONS COMPRISED THEREOF

(75) Inventors: Laurence Clary, La Colle sur Loup (FR); Pascal Collette, Le Cannet (FR); Michel Rivier, Nice (FR); Andre Jomard, Saint Vallier de Thiey (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 11/149,551

(22) Filed: Jun. 10, 2005

(65) Prior Publication Data

US 2006/0009484 A1    Jan. 12, 2006

Related U.S. Application Data

(63) Continuation of application No. PCT/EP03/015010, filed on Dec. 11, 2003.

(60) Provisional application No. 60/434,382, filed on Dec. 19, 2002.

(30) Foreign Application Priority Data

Dec. 12, 2002    (FR)    .................................. 02 15751

(51) Int. Cl.
| | |
|---|---|
| A61K 8/02 | (2006.01) |
| A61K 31/5375 | (2006.01) |
| A61K 31/41 | (2006.01) |
| A61K 31/433 | (2006.01) |
| A61K 31/4245 | (2006.01) |
| A61K 31/085 | (2006.01) |
| A61K 47/12 | (2006.01) |

(52) U.S. Cl. .................. 514/234.8; 514/544; 514/784; 514/619; 514/364; 514/381; 514/319; 514/362; 514/237.5; 424/401; 546/206; 546/194; 548/143; 548/254; 548/135; 548/360.1

(58) Field of Classification Search .......... 514/544, 514/784, 234.8, 619, 364, 381, 319, 362, 514/237.5; 546/206, 194; 548/143, 254, 548/360.1, 135
See application file for complete search history.

(56) References Cited

U.S. PATENT DOCUMENTS 5,739,169 A    4/1998   Ocain et al.

FOREIGN PATENT DOCUMENTS

WO    WO 02/12210 A1    2/2002

OTHER PUBLICATIONS

Amakura, et al., "Acalyphidins M1, M2 and D1, ellagitannins from Acalypha hispida", Phytochemistry 50(4), 1999, pp. 667-675.*
XP-002278151, Copyright 1988-2001 Beilstein Institut zur Foerderung der Chemischen Wissenschaften.
French Search Report corresponding to FR 02/15751 issued on Aug. 20, 2003, 3 pages.

* cited by examiner

Primary Examiner—Kamal A. Saeed
Assistant Examiner—Michael P. Barker
(74) Attorney, Agent, or Firm—Buchanan Ingersoll & Rooney, PC

(57) ABSTRACT

Novel polycyclic compounds having the structural formula (I) below:

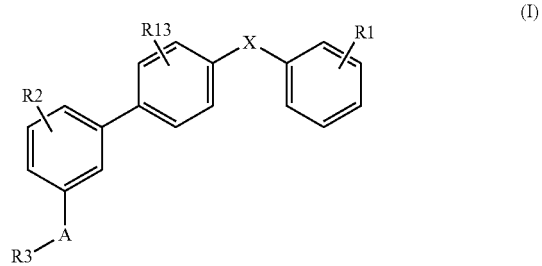

Figure 1:
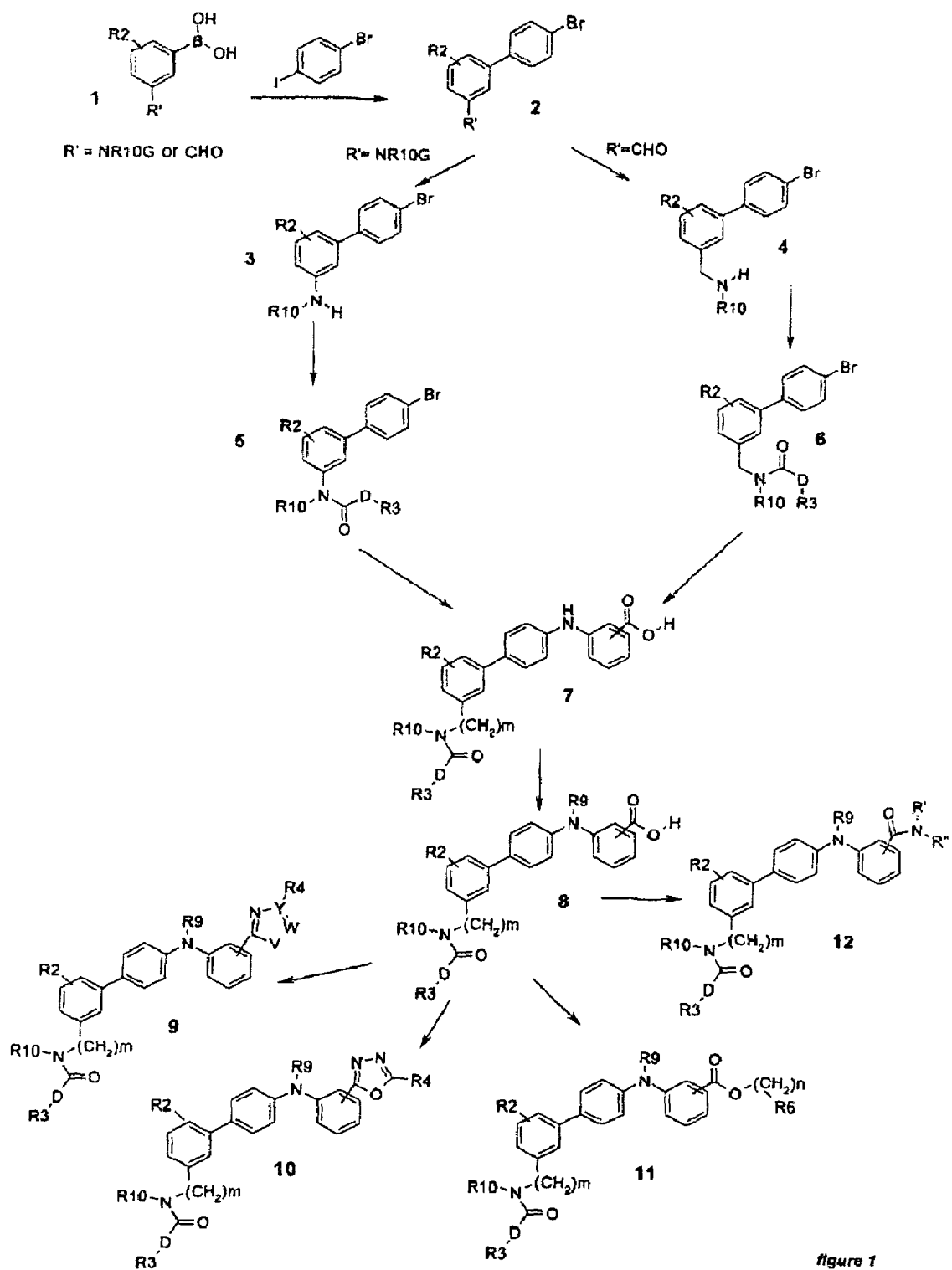

are formulated into pharmaceutical compositions suited for administration in human or veterinary medicine (in dermatology, and also in the fields of cardiovascular diseases, immune diseases and/or diseases associated with lipid metabolism), or, alternatively, into cosmetic compositions.

23 Claims, 3 Drawing Sheets

POLYCYCLIC COMPOUNDS WHICH MODULATE PPARγ TYPE RECEPTORS AND COSMETIC/PHARMACEUTICAL COMPOSITIONS COMPRISED THEREOF

CROSS-REFERENCE TO PRIORITY/PCT/PROVISIONAL APPLICATIONS

This application claims priority under 35 U.S.C. § 119 of FR 02/15751, filed Dec. 12, 2002, and of provisional application Ser. No. 60/434,382, filed Dec. 19, 2002, and is a continuation of PCT/EP 2003/015010, filed Dec. 11, 2003 and designating the United States (published in the English language on Jun. 24, 2004 as WO 2004/052840 A1); each hereby expressly incorporated by reference and each assigned to the assignee hereof.

BACKGROUND OF THE INVENTION

1. Technical Field of the Invention

The present invention relates to a novel class of polycyclic compounds which are modulators of receptors of Peroxisome Proliferator-Activated Receptor type of subtype γ (PPAR-γ). This invention also relates to a process for the preparation thereof and to their formulation into pharmaceutical compositions suited for human or veterinary medicine, or alternatively for cosmetic compositions.

2. Description of Background and/or Related and/or Prior Art

The activity of receptors of PPAR type has been the subject of many studies. Mention may be made, as a guide, of the publication entitled "Differential Expression of Peroxisome Proliferator-Activated Receptor Subtypes During the Differentiation of Human Keratinocytes", Michel Rivier et al., *J. Invest. Dermatol.*, 111, 1998, pp. 1116–1121, in which are listed a large number of bibliographic references relating to receptors of PPAR type. Mention may also be made, as a guide, of the report entitled "The PPARs: From orphan receptors to Drug Discovery", Timothy M. Willson, Peter J. Brown, Daniel D. Sternbach and Brad R. Henke, *J. Med. Chem.*, 2000, Vol. 43, pp. 527–550.

PPAR receptors activate transcription by binding to elements of DNA sequences, known as peroxisome proliferator response elements (PPRE), in the form of a heterodimer with retinoid X receptors (known as RXRs).

Three subtypes of human PPARs have been identified and described: PPARα, PPARγ and PPARδ (or NUC1).

PPARα is mainly expressed in the liver, while PPARδ is ubiquitous.

PPARγ is the most extensively studied of the three subtypes. All prior art references suggest a critical role of PPARγ in regulating the differentiation of adipocytes, where it is greatly expressed. It also has a key role in systemic lipid homeostasis.

It has been described, in particular in WO 96/33724, that PPARγ-selective compounds, such as a prostaglandin-J2 or -D2, are potential active agents for treating obesity and diabetes.

Moreover, the assignee hereof has already described PPARγ compounds and/or the use thereof in the following patent applications. FR 98/02894 describes the use of PPARγ activator compounds in the preparation of a pharmaceutical composition, the composition being intended to treat skin disorders associated with an anomaly of epidermal cell differentiation. WO 01/02543 describes a novel class of PPARγ-modulating compounds.

SUMMARY OF THE INVENTION

A novel class of PPARγ-modulating compounds has now been developed that exhibit very good specific affinity for PPARγ.

Thus, the present invention features novel compounds having the general formula (I) below:

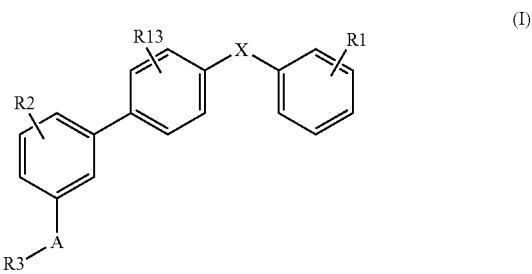

in which $R_1$ is a radical selected from among those of the following formulae (a)–(c):

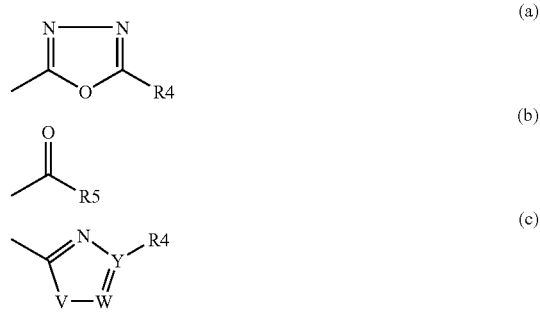

wherein $R_4$, $R_5$, V, W and Y are as defined below;

$R_2$ is a hydrogen atom, a halogen atom, an alkyl radical having from 1 to 12 carbon atoms, a hydroxyl radical, an alkoxy radical having from 1 to 7 carbon atoms, a polyether radical, a nitro radical, or an amino radical that may optionally be substituted with one or more alkyl radicals having from 1 to 12 carbon atoms, an aryl radical, an aralkyl radical, a heteroaryl radical or a heterocyclic radical; $R_3$ is a radical $-(CH_2)_t-(N-R_{15})_u-(C(O,N))_zR_{16}$, an alkyl radical having from 1 to 12 carbon atoms, an aryl radical, an aralkyl radical, a heteroaryl radical, a heterocyclic radical or a 9-fluorenylmethyl radical, wherein t, u, z, $R_{15}$ and $R_{16}$ are as defined below; $R_4$ is a hydrogen atom, an alkyl radical having from 1 to 12 carbon atoms, an aryl radical, an aralkyl radical, a heteroaryl radical or a heterocyclic radical; $R_5$ is a radical $O-(CH_2)_n-R_6$, a radical $NR'-(CH_2)_n-R_{14}$, a hydroxyl radical, an alkoxy radical having from 1 to 7 carbon atoms, an aryl radical, an aralkyl radical, a heteroaryl radical or a heterocyclic radical, or a radical:

wherein $R_6$, $R_{14}$, R', R" and n are as defined below; R' is a hydrogen atom, an alkyl radical having from 1 to 12 carbon atoms, a hydroxyl radical, an aryl radical, an aralkyl radical, a heteroaryl radical or a heterocyclic radical; R" is a hydrogen atom, an alkyl radical having from 1 to 12 carbon atoms, an aryl radical, an aralkyl radical, a heteroaryl radical, a heterocyclic radical or a radical —$(CH_2)_n$—$R_6$, wherein $R_6$ and n are as defined below; $R_6$ is an aryl radical, an aralkyl radical, a heteroaryl radical, a heterocyclic radical, a radical NH—CO—$R_7$, a radical NH—CO—O—$R_7$ or a radical N—$R_7R_8$, wherein $R_7$ and $R_8$ are as defined below; n has the values 1, 2 or 3; $R_7$ is a hydrogen atom, an alkyl radical having from 1 to 12 carbon atoms, an aryl radical, an aralkyl radical, a heteroaryl radical or a heterocyclic radical; $R_8$ is a hydrogen atom or an alkyl radical having from 1 to 3 carbon atoms; X is an oxygen or sulfur atom, or a methylene ($CH_2$) or $NR_9$ radical, wherein $R_9$ is a hydrogen atom, an alkyl radical having from 1 to 12 carbon atoms or an aralkyl radical; A is a linking radical having the following structure:

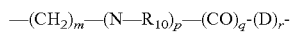   a)

or

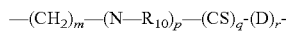   b)

wherein D, r, q, p and m are as defined below and $R_{10}$ is also as defined below; D is an oxygen or sulfur atom, a radical $NR_{11}$ or a $CH_2$ radical, wherein $R_{11}$ is as defined below; m, p, q and r, which may be identical or different, each has the values 0 or 1; $R_{10}$ and $R_{11}$, which may be identical or different, are each a hydrogen atom or an alkyl radical having from 1 to 12 carbon atoms; V is an oxygen, sulfur or nitrogen atom, the nitrogen atom being bonded to a hydrogen atom or an alkyl radical having from 1 to 6 carbon atoms; W is a nitrogen atom or a radical C—$R_{12}$, wherein $R_{12}$ is as defined below; Y is a nitrogen atom or a carbon atom; $R_{12}$ is a hydrogen atom, an alkyl radical having from 1 to 12 carbon atoms, an aryl radical, an aralkyl radical, a heteroaryl radical or a heterocyclic radical; $R_{13}$ is a hydrogen or halogen atom; $R_{14}$ is a heterocyclic radical; $R_{15}$ is a hydrogen atom, an alkyl radical having from 1 to 12 carbon atoms, an aryl radical, an aralkyl radical, a heteroaryl radical or a heterocyclic radical; t, u and z, which may be identical or different, each has a value from 0 to 4; $R_{16}$ is a hydrogen atom, an alkyl radical having from 1 to 12 carbon atoms, an aryl radical, an aralkyl radical, a heteroaryl radical, a heterocyclic radical, a radical $NHCOR_7$, a radical $NHCOOR_7$ or a radical $NR_7R_8$, wherein $R_7$ and $R_8$ are as defined above, with the proviso that, when m is 0, then q is 1 and $R_{10}$ is an alkyl radical having from 1 to 12 carbon atoms; and the optical and geometrical isomers and salts of said compounds of formula (I).

DETAILED DESCRIPTION OF BEST MODE AND SPECIFIC/PREFERRED EMBODIMENTS OF THE INVENTION

In particular, when the compounds according to the invention are in the form of salts, they are salts of an alkali metal or alkaline-earth metal, zinc salts or salts of an organic amine.

According to the present invention, the term "hydroxyl radical" means an —OH radical.

According to the present invention, the expression "alkyl radical having from 1 to 3 carbon atoms" means a methyl, ethyl or propyl radical.

According to the present invention, the expression "alkyl radical having from 1 to 12 carbon atoms" means a linear or cyclic, optionally branched, hydrogen-containing or fluorine-containing radical having 1 to 12 carbon atoms, which may be interrupted with a hetero atom, and the alkyl radicals having from 1 to 12 carbon atoms are preferably methyl, ethyl, isopropyl, butyl, tert-butyl, hexyl, octyl, decyl or cyclohexyl radicals.

The term "polyether radical" means a polyether radical having from 1 to 6 carbon atoms interrupted with at least one oxygen atom, such as methoxymethoxy, ethoxymethoxy or methoxyethoxymethoxy radicals.

The term "halogen atom" means a fluorine, chlorine or bromine atom.

The term "alkoxy radical having from 1 to 7 carbon atoms" means a radical having from one to seven carbon atoms, such as methoxy, ethoxy, isopropyloxy, tert-butoxy, hexyloxy, benzyloxy or phenoxy radicals, which may optionally be substituted with an alkyl radical having from 1 to 12 carbon atoms.

The term "aryl radical" means a phenyl, biphenyl, cinnamyl or naphthyl radical, which may be mono- or disubstituted with a halogen atom, a $CF_3$ radical, an alkyl radical having from 1 to 12 carbon atoms, an alkoxy radical having from 1 to 7 carbon atoms, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

The term "aralkyl radical" means a benzyl, phenethyl or 2-naphthylmethyl radical, which may be mono- or disubstituted with a halogen atom, a $CF_3$ radical, an alkyl radical having from 1 to 12 carbon atoms, an alkoxy radical having from 1 to 7 carbon atoms, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

The term "heteroaryl radical" means an aryl radical interrupted with one or more hetero atoms, such as a pyridyl, furyl, thienyl, isoxazolyl, oxadiazolyl, oxazolyl, isothiazolyl, quinazolinyl, benzothiadiazolyl, benzimidazolyl, indolyl or benzofuryl radical, optionally substituted with at least one halogen, an alkyl radical having from 1 to 12 carbon atoms, an alkoxy radical having from 1 to 7 carbon atoms, an aryl radical, a nitro function, a polyether radical, a heteroaryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl radical having from 1 to 12 carbon atoms.

The term "heterocyclic radical" preferably means a morpholino, piperidino, piperazino, 2-oxo-1-piperidyl or 2-oxo-1-pyrrolidinyl radical, optionally substituted with at least one alkyl radical having from 1 to 12 carbon atoms, an alkoxy radical having from 1 to 7 carbon atoms, an aryl radical, a nitro function, a polyether radical, a heteroaryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl radical having from 1 to 12 carbon atoms.

Among the compounds of formula (I) within the scope of the present invention, mention may be made especially of the following compounds (alone or as a mixture):

1. 2-[3'-({[6-(2-Methoxyethoxymethoxy)naphthalene-2-carbonyl]methylamino}methyl)biphenyl-4-ylamino]methyl benzoate;
2. 2-[3'-({[6-(2-Methoxyethoxymethoxy)naphthalene-2-carbonyl]methylamino}methyl)biphenyl-4-ylamino]benzoic acid;
3. N-{4'-[2-(2,5-Difluorobenzylcarbamoyl)phenylamino]biphenyl-3-ylmethyl}-N-methyl-6-(2-methoxyethoxymethoxy)naphthalene-2-carboxylamide;
4. N-{4'-[2(Benzylmethylcarbamoy)phenylamino]biphenyl-3-ylmethyl}-N-methyl-6-(2-methoxyethoxymethoxy)naphthalene-2-carboxylamide;
5. 2-{3'-[(Methyloctanoylamino)methyl]biphenyl-4-ylamino}methyl benzoate;
6. 2-{3'-[(Methyloctanoylamino)methyl]biphenyl-4-ylamino}benzoic acid;
7. 2-(Methyl-{3'-[(methyloctanoylamino)methyl]biphenyl-4-yl}amino)methyl benzoate;
8. 2-(Methyl-{3'-[(methyloctanoylamino)-methyl]biphenyl-4-yl}amino)benzoic acid;
9. N-(3-Methylbutyl)-2-{3'-[(methyloctanoylamino)methyl]biphenyl-4-ylamino}benzamide;
10. N-Methyl-N-{4'-[2-(5-propyl-[1,3,4]oxadiazol-2-yl)phenylamino]biphenyl-3-ylmethyl}octanoylamide;
11. N-Methyl-N-{4'-[2-(1H-tetrazol-5-yl)phenylamino]biphenyl-3-ylmethyl}octanoylamide;
12. 3-[3'({(6-(2-Methoxyethoxymethoxy)naphthalene-2-carbonyl]methylamino}methyl)biphenyl-4-ylamino]ethyl benzoate;
13. 3-[3'-({[6-(2-Methoxyethoxymethoxy)naphthalene-2-carbonyl]methylamino}methyl)biphenyl-4-ylamino]benzoic acid;
14. 3-(3'-{[(6-Hydroxynaphthalene-2-carbonyl)methylamino]methyl}biphenyl-4-ylamino)ethyl benzoate;
15. 3-(3'-{[(6-Hydroxynaphthalene-2-carbonyl)methylamino]methyl}biphenyl-4-ylamino)benzoic acid;
16. N-Methyl-N-{4'-[3-(4-methylpiperidine-1-carbonyl)-phenylamino]biphenyl-3-ylmethyl}6-(2-methoxyethoxymethoxy)naphthalene-2-carboxylamide;
17. N-Methyl-N-{4'[3-(morpholine-4-carbonyl)-phenylamino]biphenyl-3-ylmethyl}-6-(2-methoxyethoxymethoxy)naphthalene-2-carboxylamide;
18. N-Methyl-N-{4'-[3-(4-methylpiperidine-1-carbonyl)phenylamino]bipheny-3-ylmethyl}-6-hydroxynaphthalene-2-carboxylamide;
19. N-Methyl-N-{4'[3-(morpholine-4-carbonyl)phenylamino]biphenyl-3-ylmethyl}-6-hydroxynaphtalene-2-carboxylamide;
20. 3-{3'-[(Methyloctanoylamino)methyl]biphenyl-4-ylamino}benzoic acid;
21. 2-{3'-[(Methyloctanoylamino)methyl]biphenyl-4-yloxy}ethyl benzoate;
22. 2-{3'-[(Methyloctanoylamino)methyl]biphenyl-4-yloxy}benzoic acid;
23. 2-[3'-(1-Methyl-3-naphthalene-2-ylureido)biphenyl-4-ylamino]benzoic acid;
24. 2-{[3'-(3-Heptyl-1-methylureido)biphenyl-4-yl]methylamino}benzoic acid;
25. 2-(3'-{[Methyl(quinoxaline-6-carbonyl)amino]methyl}biphenyl-4-ylamino)benzoic acid;
26. 2-(3'-{[(2-1H-Benzoimidazol-2-ylacetyl)methylamino]methyl}biphenyl-4-ylamino)benzoic acid;
27. 2-[3'-(1-Methyl-3-thiophene-3-ylureido)biphenyl-4-ylamino]benzoic acid;
28. 2-[3'-(3-Benzo[1,2,5]thiadiazol-5-yl-1-methylureidobiphenyl-4-ylamino]benzoic acid;
29. 1-Methyl-1-{4'-[3-(morpholine-4-carbonyl)phenylamino]bipheny-3-yl}-3-naphth-2-yl-urea;
30. N-Methyl-3-[3'-(1-methyl-3-naphth-2-ylureido)biphenyl-4-ylamino]-N-phenethylbenzamide;
31. 3-{Methyl-[3'-(1-methyl-3-naphth-2-ylureido)biphenyl-4-yl]amino}benzoic acid;
32. 3-(3'-{[Methyl(quinoxaline-6-carbonyl)-amino]methyl}biphenyl-4-ylamino)isobutyl benzoate;
33. 3-[3'-({[6-(2-Methoxyethoxymethoxy)naphthalene-2-carbonyl]methylamino}methyl)biphenyl-4-ylmethyl]benzoic acid;
34. 2-{3'[3-(4-Dimethylaminophenyl)-1-methylureido]biphenyl-4-ylsulfanyl}benzoic acid;
35. 2-[3'-(3-Benzo[1,2,5]thiadiazol-5-yl-1-methylureido)biphenyl-4-yloxy]benzoic acid;
36. 2-Morpholin-4-ylethyl 3-(3'-{[methyl(quinoxaline-6-carbonyl)amino]methyl}biphenyl-4-yloxy)benzoate;
37. N-{4'[3-(2-Dimethylaminoethylcarbamoyl)phenoxy]biphenyl-3-ylmethyl}-N-methyl-6-(2-methoxyethoxy)naphthalene-2-carboxylamide;
38. 3-[3'-({[6-(2-Methoxyethoxymethoxy)naphthalene-2-carbonyl]amino}methyl)biphenyl-4-ylamino]benzoic acid;
39. 3-{3'-[6-(2-Methoxyethoxymethoxy)naphth-2-yloxycarbonylmethyl]biphenyl-4-ylamino}benzoic acid;
40. 2-[3'-(3-Heptyl-1-methylureido)biphenyl-4-ylamino]benzoic acid;
41. 3-Heptyl-1-methyl-1-{4'-[2-(morpholine-4-carbonyl)phenylamino]biphenyl-3-yl}-urea;
42. 3-Heptyl-1-methyl-1-(4'-{methyl-[2-(morpholine-4-carbonyl)phenyl]amino}biphenyl-3-yl)urea;
43. 3-Heptyl-1-methyl-1-(4'-{methyl-[2-(4-methylpiperidine-1-carbonyl)phenyl]amino}biphenyl-3-yl)urea;
44. 3-Heptyl-1-methyl-1-{4'-[2-(4-methylpiperidine-1-carbonyl)phenylamino]biphenyl-3-yl}urea;
45. 2-[3'-(3-Heptyl-1-methylureido)biphenyl-4-ylsulfanyl]benzoic acid;
46. 2-[3'-(3-Heptyl-1-methylureido)biphenyl-4-ylmethyl]benzoic acid;
47. 2-[3'-(1-Methyl-3-pentylureido)biphenyl-4-ylamino]benzoic acid;
48. 1-Methyl-1-{4'-[2-(morpholine-4-carbonyl)phenylamino]biphenyl-3-yl}-3-pentylurea;
49. 2-[3'-(3-Heptyl-1-methylthioureido)biphenyl-4-ylamino]benzoic acid;
50. 3-Hepty-1-methyl-1-{4'-[2-(5-propyl-[1,3,4]oxadiazol-2-yl)phenylamino]biphenyl-3-yl}urea;
51. 3-Heptyl-1-methyl-1-{4'-[2-(1H-tetrazol-5-yl)phenylamino]biphenyl-3-yl}urea;
52. 2-{3'-[(Hexanoylmethylamino)methyl]biphenyl-4-ylamino}benzoic acid;
53. N-Methyl-N-{4'-[2-(morpholine-4-carbonyl)phenylamino]biphenyl-3-ylmethyl}hexanoylamide;
54. 2-(3'-{[Methyl-(5-oxohexanoy)amino]methyl}biphenyl-4-ylamino)benzoic acid;
55. 2-(3'-{[Methyl-(4-methylaminobutyryl)amino]methyl}biphenyl-4-ylamino)benzoic acid;
56. 2-[3'-({[3-(N',N'-Dimethyl-hydrazinocarbonyl)propionyl]methylamino}methyl)-biphenyl-4-ylamino]benzoic acid;
57. 2-[3'(3-Heptyl-1-methylureido)biphenyl-4-ylamino]-N-hydroxybenzamide;
58. 2-[3-Fluoro-3'-(3-heptyl-1-methylureido)biphenyl-4-ylamino]benzoic acid;

59. 2-[3-Fluoro-3'-(1-methyl-3-pentylureido)biphenyl-4-ylamino]benzoic acid;
60. 2-[2-Fluoro-3'-(1-methyl-3-pentylureido)biphenyl-4-ylamino]benzoic acid;
61. 2-[2-Fluoro-3'-(3-heptyl-1-methylureido)biphenyl-4-ylamino]benzoic acid;
62. N-Methyl-N-{4'-[3-(2-piperidin-1-ylethylcarbamoyl)phenylamino]biphenyl-3-ylmethyl}-6-(2-methoxy-ethoxymethoxy)naphthalene-2-carboxylamide;
63. N-Methyl-N-{4'-[3-(2-morpholin-4-ylethylcarbamoyl)-phenylamino]biphenyl-3-ylmethyl}-6-(2-methoxy-ethoxymethoxy)naphthalene-2-carboxylic acid amide;
64. N-Methyl-N-{4'-[2-(morpholine-4-carbonyl)phenylamino]biphenyl-3-ylmethyl}-6-(2-methoxy-ethoxymethoxy)naphthalene-2-carboxylic acid amide;
65. N-Methyl-N-{4'-[2-(4-methylpiperidine-1-carbonyl)phenylamino]biphenyl-3-ylmethyl}-6-(2-methoxy-ethoxymethoxy)naphthalene-2-carboxylamide;
66. 2-(3'-{[(6-Hydroxynaphthalene-2-carbonyl)methylamino]methyl}biphenyl-4-ylamino)benzoic acid;
67. 2-[3'-(3-Hexyl-1-methylthioureido)biphenyl-4-ylamino]benzoic acid;
68. 2-{3'-[(Methyloctanethioylamino)methyl]biphenyl-4-ylamino}benzoic acid;
69. 2-{4'-Fluoro-3'-[(methyloctanoylamino)methyl]biphenyl-4-ylamino}benzoic acid;
70. 2-{2'-Fluoro-5'-[(methyloctanoylamino)methyl]biphenyl-4-ylamino}benzoic acid;
71. 3-Heptyl-1-methyl-1-{4'-[2-(pyrazole-1-carbonyl)phenylamino]biphenyl-3-yl}urea;
72. 2-(3'-{[Methyl-(1,4,5,6-tetrahydrocyclopentapyrazole-3-carbonyl)amino]methyl}biphenyl-4-ylamino)benzoic acid;
73. 2-(3'-{[Methyl-(2-methylthiazolidine-4-carbonyl)methyl}biphenyl-4-ylamino)benzoic acid;
74. 2-[3'-({[Methyl-[2-(3-methylbenzoylamino)acetyl]amino}methyl)biphenyl-4-ylamino]benzoic acid;
75. 2-(3'-{[Methyl-(3-phenylpropionyl)amino]methyl}biphenyl-4-ylamino)benzoic acid;
76. 2-{3'-[(Methyloctanoylamino)methyl]biphenyl-4-ylamino}-N-(2-morpholin-4-ylethyl)benzamide;
77. 2-(3'-{[(9H-Fluoren-9-ylmethoxycarbonyl)methylamino]methyl}biphenyl-4-ylamino)benzoic acid;
78. N-Methyl-N-{4'-[2-(4-methylimidazole-1-carbonyl)phenylamino]biphenyl-3-ylmethyl}octanoylcarboxylamide;
79. 1-[4'-(2-Benzoylphenylamino)biphenyl-3-yl]-3-heptyl-1-methylurea;
80. 2-[3'-(3-Heptyl-1-methylureido)biphenyl-4-ylamino]-N-methyl-N-piperidin-1-ylbenzamide;
81. 2-[3'-(3-Heptyl-1-methylureido)biphenyl-4-ylamino]-N-methyl-N-phenyl-benzamide.

According to the present invention, the compounds of formula (I) that are more particularly preferred are those having at least one of the following characteristics:

$R_1$ is a radical of formula (b), in which $R_5$ is preferably a hydroxyl group, a heterocyclic radical or NR'R";

A is a linking radical of structure —CH$_2$N(R$_{10}$)—CO or —N(R$_{10}$)—CO-(D) wherein r=0 or 1;

$R_3$ is an alkyl, aryl or heteroaryl radical;

X is an oxygen atom or a radical NR$_9$ in which $R_9$ is preferably a hydrogen atom or an alkyl radical having from 1 to 4 carbon atoms.

According to one particular embodiment of the invention, the compounds of formula (I) are such that:

$R_1$ is a radical of formula (b) in which $R_5$ is a hydroxyl group;

A is a linking radical of structure —N(R$_{10}$)—CO-(D)$_r$ wherein r=1 and D=NR$_{11}$;

$R_3$ is an alkyl radical having from 1 to 12 carbon atoms;

X is a radical NR$_9$.

According to another particular embodiment of the invention, the compounds of formula (I) are such that:

$R_1$ is a radical of formula (b) in which $R_5$ is a heterocyclic radical or NR'R";

A is a linking radical of structure —N(R$_{10}$)—CO-(D) wherein r=1 and D=NR$_{11}$;

$R_3$ is an alkyl radical having from 1 to 12 carbon atoms;

X is a radical NR$_9$.

A general description of the preparation of the compounds of general formulae 7 to 12, 20 to 24 and 30 to 34 of Figures of Drawing 1, 2 and 3 is given below.

The reaction scheme described in FIG. 1 is a general scheme for obtaining derivatives in which X corresponds to NR$_9$.

The intermediate 2 is obtained via a Suzuki coupling between the boronic acid 1 (obtained according to the standard method for obtaining boronic acids from optionally protected N-alkyl-3-bromoaniline or from 3-bromobenzaldehyde) and 4-iodobromobenzene, catalyzed, for example, with tetrakis(triphenylphosphino)palladium.

When R'=CHO, compound 2 gives compound 4 via an aminative reduction reaction with an amine HNR$_{10}$.

Compounds 5 and 6 are obtained after deprotecting the amine (if necessary) via addition to an isocyanate R$_3$—N=C=O or condensation with an acid or an acid halide.

The intermediates 7 are prepared via a Buchwald reaction, in the presence of a palladium-based catalyst (for example palladium (II) acetate or tris(dibenzylideneacetone)dipalladium(0)) of a ligand molecule (for example rac-2,2'-bis (diphenylphosphino)-1,1'-binaphthyl:BINAP) and a base (sodium tert-butoxide or caesium carbonate) in toluene at 100° C., followed by a saponification reaction.

The heterocyclic compounds 9 and 10 are synthesized via standard methods for synthesizing heterocycles, with, in the case of compound 10 (with R$_4$=n-propyl), for example, condensation of butyric hydrazide and cyclization with heating to 105° C. in the presence of phosphorus oxychloride.

The esters 11 may be prepared, for example, via esterification with alcohols HO(CH$_2$)$_n$R$_6$.

The compounds 12 are obtained via an amidation reaction with an amine of aliphatic or cyclic HNR'R" type.

Figure 2:
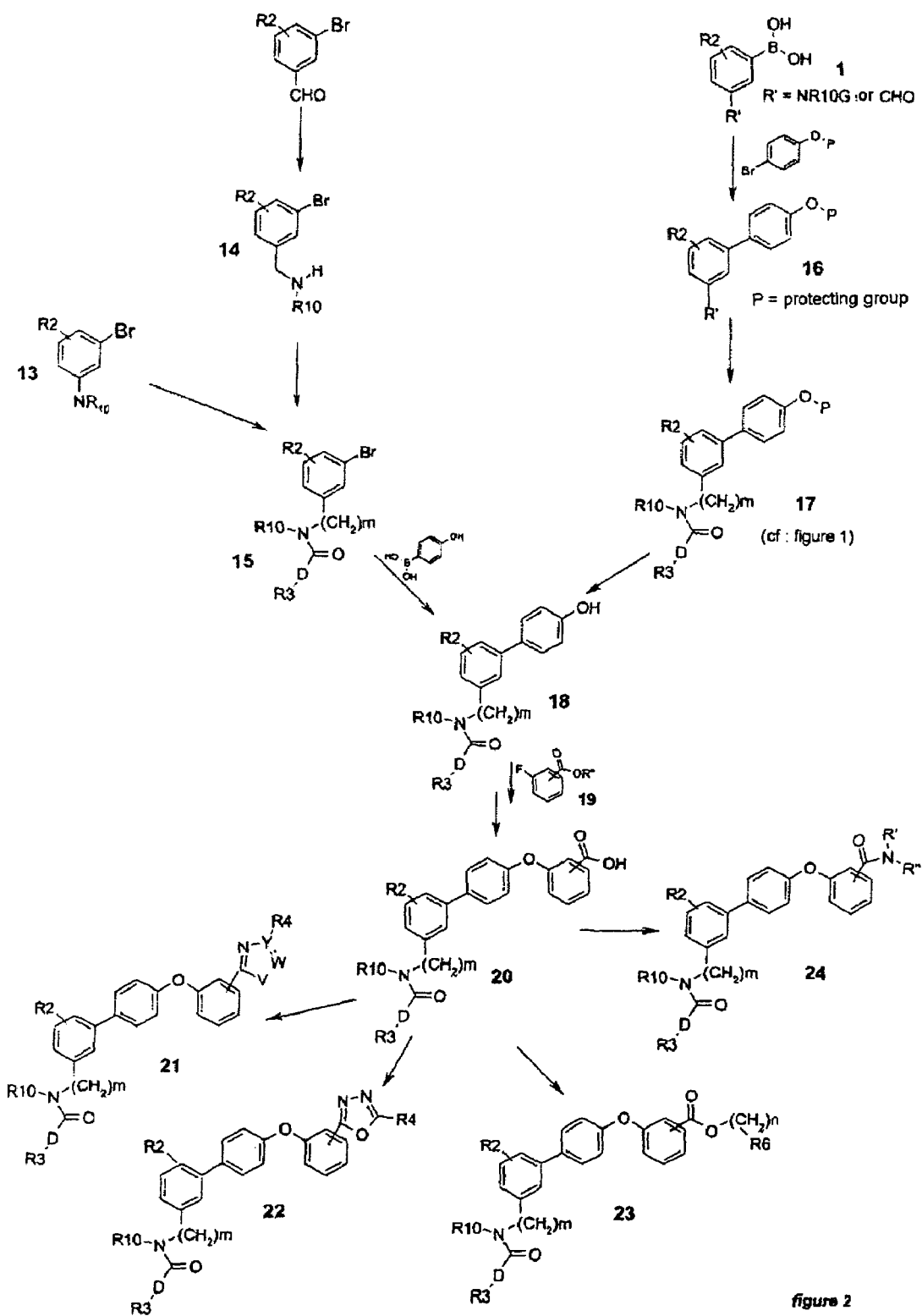

For the preparation of the compounds corresponding to the general formula with X=O, the reaction scheme is described in FIG. 2.

The intermediate 18 may be obtained according to two routes:

via a Suzuki reaction between compound 15 and 4-hydroxybenzeneboronic acid prepared beforehand. As described in FIG. 1, compound 15 is obtained from compounds 13 and 14 via addition to an isocyanate R$_3$—N=C=O or condensation with an acid or an acid halide, or via a deprotection reaction of compound 17, obtained beforehand via a Suzuki reaction between the boronic acid 1 and protected 4-bromophenol, followed by condensation with an acid or an acid halide or addition to an isocyanate R$_3$—N=C=O.

Compound 18 gives compound 20 via a coupling reaction with the fluoro derivative 19 in the presence of a base (for example potassium carbonate) in a polar solvent (dimethylacetamide), followed by a saponification reaction.

Compounds 21 to 24 are obtained according to the standard methods used for obtaining derivatives 9 to 12.

Figure 3:
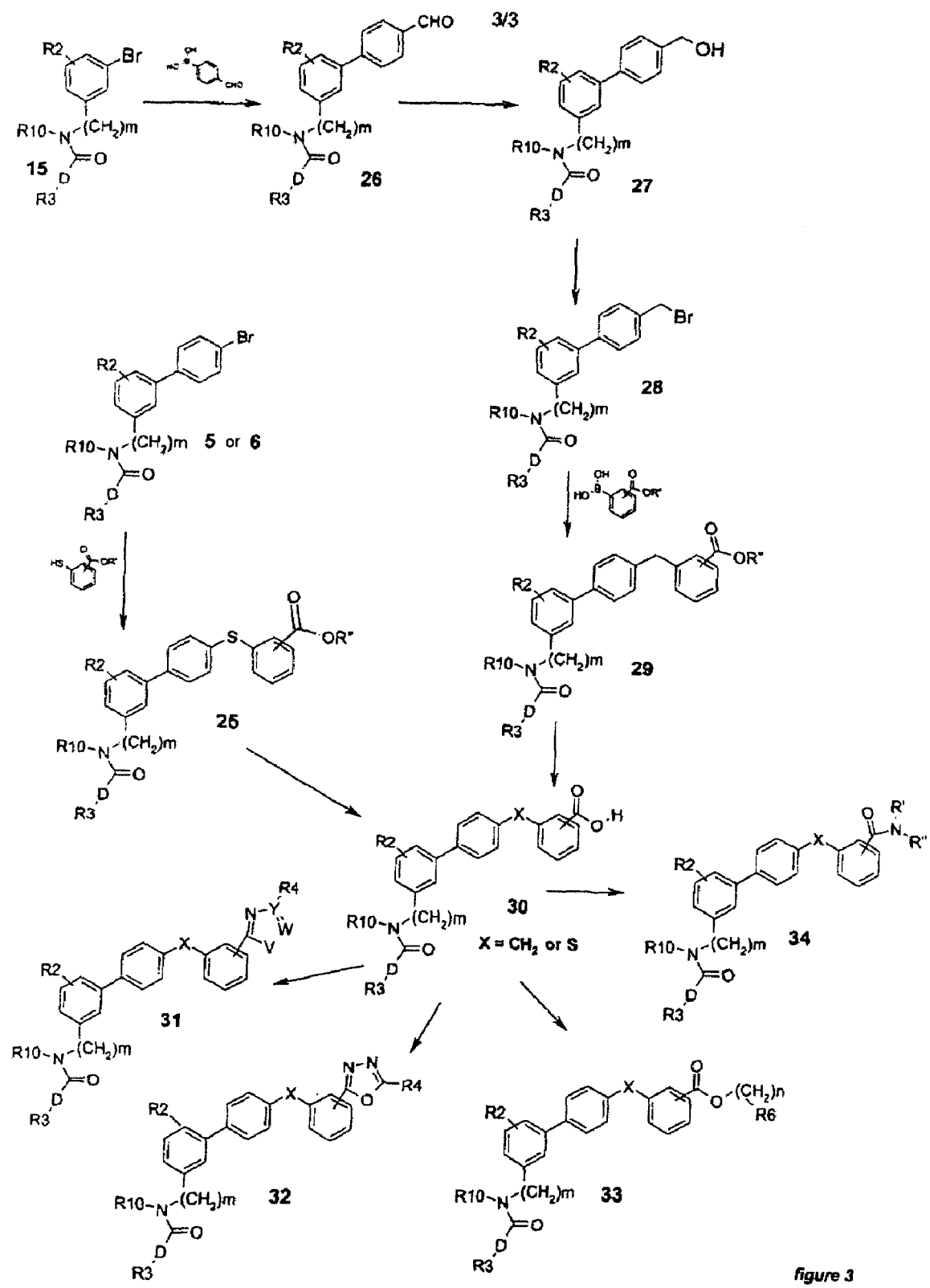

The preparation of the compounds for which X=S or $CH_2$ in the general formula is described by FIG. 3.

The intermediate 25 is obtained via a coupling reaction between the derivative 5 or 6 (their synthesis is described in FIG. 1) and a commercial methyl mercaptobenzoate, in the presence of a reducing agent (for example sodium borohydride) and a nickel-based catalyst ($NiBr_2$bipy).

Compound 26 is obtained via a Suzuki coupling between compound 15 (described in FIG. 2) and 4-formylbenzeneboronic acid.

Via reduction of the aldehyde function to an alcohol with sodium tetraborohydride in methanol, the intermediate 27 is obtained.

The derivative 28 is prepared via bromination of compound 27 with carbon tetrabromide, for example, in the presence of triphenylphosphine.

A Suzuki reaction between the derivative 28 and a commercial methoxycarbonylphenolboronic acid, catalyzed with tetrakis(triphenylphosphino)palladium, in ethylene glycol dimethyl ether gives compound 29.

The saponification of compounds 25 and 29 allows the production of the derivative of general formula 30. The production of compounds 31 to 34 is performed according to the standard methods described for derivatives 9 to 12.

The compounds according to the invention exhibit modulatory properties on receptors of PPAR type. This activity on the PPARα, δ and γ receptors is measured in a transactivation test and quantified via the dissociation constant Kdapp (apparent), as described in Example 23.

The preferred compounds of the present invention have a dissociation constant Kdapp of less than or equal to 1000 nM and advantageously less than or equal to 500 nM.

Preferably, the compounds are modulators of receptors of specific PPARγ type, i.e., they have a ratio between the Kdapp for the PPARα and PPARδ receptors, and the Kdapp for the PPARγ receptors, of greater than or equal to 10. Preferably, this ratio PPARγ/PPARα or PPARγ/PPARδ is greater than or equal to 50 and more advantageously greater than or equal to 100.

The present invention also features medicinal products comprising the compounds of formula (I) as described above.

The present invention also features administration of the compounds of formula (I) for regulating and/or restoring the metabolism of skin lipids.

The compounds according to the invention are particularly suitable in the following fields of treatment:
1) for treating dermatological afflictions or conditions associated with a keratinization disorder relating to differentiation and to proliferation, in particular for treating common acne, comedones, polymorphs, rosacea, nodulocystic acne, acne conglobata, senile acne and secondary acne such as solar, medicinal or occupational acne,
2) for treating other types of keratinization disorder, in particular ichthyosis, ichthyosiform conditions, Darrier's disease, palmoplantar keratoderma, leukoplakia and leukoplakiform conditions, and cutaneous or mucous (oral) lichen,
3) for treating other dermatological afflictions or conditions having an inflammatory immuno-allergic component, with or without a cellular proliferation disorder, and in particular all forms of psoriasis, whether cutaneous, mucous or ungual psoriasis, and even psoriatic arthritis, or alternatively cutaneous atopy such as eczema, or respiratory atopy or gingival hypertrophy,
4) for treating all dermal or epidermal proliferations, whether benign or malignant, whether or not of viral origin, such as common warts, flat warts and epidermodysplasia verruciformis, oral or florid papillomatoses, T lymphoma and proliferations which may be induced by ultraviolet light, in particular in the case of basal cell and spinocellular epithelioma, and also any precancerous skin lesion such as keratoacanthomas,
5) for treating other dermatological disorders such as immune dermatitides, such as lupus erythematosus, bullous immune diseases and collagen diseases, such as scleroderma,
6) in the treatment of dermatological or systemic afflictions or conditions having an immunological component,
7) in the treatment of skin disorders due to exposure to UV radiation, and also for repairing or combating aging of the skin, whether light-induced or chronological aging, or for reducing actinic keratoses and pigmentations, or any pathology associated with chronological or actinic aging, such as xerosis,
8) for combating sebaceous function disorders such as the hyperseborrhoea of acne or simple seborrhoea or seborrhoeic dermatitis,
9) for preventing or treating cicatrization disorders or for preventing or repairing stretch marks,
10) in the treatment of pigmentation disorders, such as hyperpigmentation, melasma, hypopigmentation or vitiligo,
11) in the treatment of lipid metabolism afflictions or conditions, such as obesity, hyperlipidaemia, non-insulin-dependent diabetes or syndrome X,
12) in the treatment of inflammatory afflictions or conditions such as arthritis,
13) in the treatment or prevention of cancerous or precancerous conditions,
14) in the prevention or treatment of alopecia of various origins, in particular alopecia caused by chemotherapy or radiation,
15) in the treatment of immune system disorders, such as asthma, type I sugar diabetes, multiple sclerosis or other selective dysfunctions of the immune system, or
16) in the treatment of afflictions or conditions of the cardiovascular system, such as arteriosclerosis or hypertension.

The present invention also features pharmaceutical or cosmetic compositions comprising, in a physiologically acceptable medium, at least one compound of formula (I) as defined above.

The compositions according to the invention may be administered orally, enterally, parenterally, topically or ocularly. The pharmaceutical composition is preferably packaged in a form which is suitable for topical application.

Via the oral route, the composition, more particularly the pharmaceutical composition, may be in the form of tablets, gel capsules, sugar-coated tablets, syrups, suspensions, solutions, powders, granules, emulsions or lipid or polymer vesicles or nanospheres or microspheres to allow controlled release. Via the parenteral route, the composition may be in the form of solutions or suspensions for infusion or for injection.

The compounds according to the invention are generally administered at a daily dose of about 0.001 mg/kg to 100 mg/kg of body weight in 1 to 3 dosage intakes.

The compounds are used systemically at a concentration generally from 0.001% to 10% by weight and preferably from 0.01% to 1% by weight relative to the weight of the composition.

Via the topical route, the pharmaceutical composition according to the invention is more particularly intended for treating the skin and mucous membranes and may be in the form of ointments, creams, milks, salves, powders, impregnated pads, syndets, solutions, gels, sprays, foams, suspensions, stick lotions, shampoos or washing bases. It may also be in the form of suspensions of lipid or polymer vesicles or nanospheres or microspheres or polymer patches and hydrogels to allow controlled release. This topical-route composition may be in anhydrous form, in aqueous form or in the form of an emulsion.

The compounds are used topically at a concentration generally from 0.001% to 10% by weight, preferably from 0.01% to 1% by weight relative to the total weight of the composition.

The compounds of formula (I) according to the invention also find an application in the cosmetic field, in particular in body and hair hygiene and more particularly for regulating and/or restoring skin lipid metabolism.

This invention therefore also features the cosmetic use of a composition comprising, in a physiologically acceptable support, at least one of the compounds of formula (I) for body or hair hygiene.

The cosmetic composition according to the invention containing, in a cosmetically acceptable support, at least one compound of formula (I) or an optical or geometrical isomer thereof or a salt thereof, may usually be in the form of a cream, a milk, a lotion, a gel, suspensions of lipid or polymer vesicles or nanospheres or microspheres, impregnated pads, solutions, sprays, foams, sticks, soaps, shampoos or washing bases.

The concentration of compound of formula (I) in the cosmetic composition is from 0.001% to 3% by weight relative to the total weight of the composition.

The pharmaceutical and cosmetic compositions as described above may also contain inert or even pharmacodynamically active additives as regards the pharmaceutical compositions, or combinations of these additives, and especially:

wetting agents;
flavor enhancers;
preservatives such as para-hydroxybenzoic acid esters;
stabilizers;
humidity regulators;
pH regulators;
osmotic pressure modifiers;
emulsifiers;
UV-A and UV-B screening agents;
antioxidants, such as α-tocopherol, butylhydroxyanisole or butylhydroxytoluene, superoxide dismutase, ubiquinol or certain metal-chelating agents;
depigmenting agents such as hydroquinone, azelaic acid, caffeic acid or kojic acid;
emollients;
moisturizers, for instance glycerol, PEG 400, thiamorpholinone and derivatives thereof, or urea;
antiseborrhoeic or antiacne agents, such as S-carboxymethylcysteine, S-benzylcysteamine, salts thereof or derivatives thereof, or benzoyl peroxide;
antibiotics, for instance erythromycin and its esters, neomycin, clindamycin and its esters, and tetracyclines;
antifungal agents such as ketoconazole or polymethylene-4,5-isothiazolidones-3;
agents for promoting regrowth of the hair, for instance Minoxidil (2,4-diamino-6-piperidinopyrimidine 3-oxide) and its derivatives, Diazoxide (7-chloro-3-methyl-1,2,4-benzothiadiazine 1,1-dioxide) and Phenytoin (5,4-diphenylimidazolidine-2,4-dione);
non-steroidal anti-inflammatory agents;
carotenoids, and especially β-carotene;
antipsoriatic agents such as anthraline and its derivatives;
eicosa-5,8,11,14-tetraynoic acid and eicosa-5,8,11-triynoic acid, and esters and amides thereof;
retinoids, i.e., RAR or RXR receptor ligands, which may be natural or synthetic;
corticosteroids or oestrogens;
α-hydroxy acids and α-keto acids or derivatives thereof, such as lactic acid, malic acid, citric acid, glycolic acid, mandelic acid, tartaric acid, glyceric acid or ascorbic acid, and also the salts, amides or esters thereof, or β-hydroxy acids or derivatives thereof, such as salicylic acid and the salts, amides or esters thereof;
ion-channel blockers such as potassium-channel blockers;
or alternatively, more particularly for the pharmaceutical compositions, in combination with medicinal products known to interfere with the immune system (for example cyclosporin, FK 506, glucocorticoids, monoclonal antibodies, cytokines or growth factors, etc.).

Needless to say, one skilled in this art will take care to select the optional compound(s) to be added to these compositions such that the advantageous properties intrinsically associated with the present invention are not, or are not substantially, adversely affected by the envisaged addition.

Several examples of the production of active compounds of formula (I) according to the invention, and also biological activity results for such compounds and various specific formulations based on its compounds will now be given, it being understood that same are intended only as illustrative and in nowise limitative. In said examples to follow, all parts and percentages are given by weight, unless otherwise indicated.

EXAMPLE 1

Synthesis of methyl 2-[3'-({[6-(2-methoxy-ethoxymethoxy)naphthalene-2-carbonyl]methyl-amino}methyl)biphenyl-4-ylamino]benzoate (a) Preparation of 4'-bromobiphenyl-3-carbaldehyde:
89 ml (180 mmol) of a 2M solution of potassium carbonate are added to a solution containing 20 g (71 mmol) of p-iodobromobenzene and 14 g (92 mmol) of 3-formylbenzeneboronic acid in toluene, followed by addition of 4.1 g (3.5 mmol) of tetrakis(triphenylphosphino)palladium. The reaction medium is refluxed for 16 hours. After cooling to room temperature, water is added and the organic products are extracted with ethyl acetate. The solvents are evaporated off and the residue obtained is purified by chromatography on silica with a 99/1 heptane/ethyl acetate mixture. 6.2 g (23.6 mmol) of the expected aldehyde, an orange solid, are isolated in a yield of 33%.

(b) Preparation of (4'-bromobiphenyl-3-ylmethyl)methylamine hydrochloride:
4.5 g (66.2 mmol) of methylamine hydrochloride are introduced into a solution containing 6.2 g (23.6 mmol) of 4'-bromobiphenyl-3-carbaldehyde in
95 ml of methanol. After stirring for 10 minutes at room temperature, 2.3 g (37 mmol) of sodium cyanoborohydride are added portionwise. The reaction medium is stirred for 16 hours and water is added. The organic products are extracted with ethyl acetate. After evaporating off the solvents, the crude product is purified by chromatography on a column of silica eluted with a 95/5 heptane/ethyl acetate mixture. 1.3 g of a white solid corresponding to the desired amine are isolated. The amine hydrochloride is obtained by precipitation after dissolving in diethyl ether, followed by addition of a solution of hydrogen chloride in isopropanol. By filtration, 1.0 g (3.3 mmol) of hydrochloride is obtained in a yield of 14%.

(c) Preparation of 6-(2-methoxyethoxymethoxy)-2-naphthoic acid:

Methyl 6-hydroxynaphthalene-2-carboxylate

A solution of 15.7 g (83.4 mmol) of 6-hydroxy-2-naphthoic acid is refluxed for 8 hours in a mixture of 160 ml of methanol and 8 ml of concentrated sulfuric acid. After cooling, the product precipitates out. After filtration and washing with isopropyl ether, 14.1 g of methyl 6-hydroxynaphthalene-2-carboxylate are obtained in the form of a beige-colored solid in a yield of 84%.

Methyl 6-(2-methoxyethoxymethoxy)napthalene-2-carboxylate 3.3 g (83 mmol) of 60% sodium hydride in oil are added portionwise to a solution of 14 g (69 mmol) of methyl 6-hydroxynaphthalene-2-carboxylate in 180 ml of an equivolume mixture of tetrahydrofuran and dimethylformamide. After the evolution of gas has ceased, 8.7 ml (76 mmol) of methoxyethoxymethyl chloride are added dropwise. The reaction medium is stirred at room temperature for 3 hours, immersed into ice-cold water and extracted with ethyl ether. The organic phase is dried over sodium sulfate, filtered and concentrated under vacuum. The residue obtained is purified by chromatography on a column of silica eluted with an 80/20 heptane/ethyl acetate mixture. 17 g of methyl 6-(2-methoxyethoxymethoxy)naphthalene-2-carboxylate are obtained in the form of a colorless oil, in a yield of 85%.

6-(2-Methoxyethoxymethoxy)-2-naphthoic acid 12.9 g (325 mmol) of sodium hydroxide pellets are added to a solution of 16.9 g (58 mmol) of methyl 6-(2-methoxyethoxymethoxy)naphthalene-2-carboxylate in 200 ml of tetrahydrofuran, 20 ml of methanol and a few drops of water, and the reaction medium is stirred at room temperature for 4 hours. Next, aqueous 1N hydrochloric acid solution is added until pH=2 is obtained, and the reaction medium is extracted with ethyl acetate, dried over sodium sulfate, filtered and concentrated under vacuum. The residue obtained is washed with heptane and filtered. 14.9 g of 6-(2-methoxyethoxymethoxy)-2-naphthoic acid are obtained in the form of a white solid, in a yield of 92%.

Melting point: 110° C.

(d) Preparation of N-(4'-bromobiphenyl-3-ylmethyl)-N-methyl-6-(2-methoxyethoxymethoxy)naphthalene-2-carboxylamide:

1.1 ml (8.0 mmol) of triethylamine and 540 mg (4.0 mmol) of 1-hydroxybenzotriazole are added to a solution containing 1 g (3.6 mmol) of (4'-bromobiphenyl-3-ylmethyl)methylamine hydrochloride in 10 ml of dichloromethane. After stirring for 30 minutes at room temperature, 1 g (3.6 mmol) of 6-(2-methoxyethoxymethoxy) naphthoic acid are introduced, followed by 760 mg (4.0 mmol) of 1-(3-dimethylaminopropyl)-3-ethyl-carbodiimide hydrochloride (EDCl). The reaction medium is stirred at room temperature for 3 hours and then washed with saturated sodium chloride solution. After evaporating off the solvents, the crude product is purified by chromatography on a column of silica eluted with a 7/3 heptane/ethyl acetate mixture. 1.72 g (3.6 mmol) of the expected amide are isolated in a yield of 99%.

(e) Synthesis of methyl 2-[3'-({[6-(2-methoxyethoxymethoxy)-naphthalene-2-carbonyl]methylamino}methyl)biphenyl-4-ylamino]benzoate:

1.7 g (3.2 mmol) of N-(4'-bromobiphenyl-3-ylmethyl)-N-methyl-6-(2-methoxyethoxymethoxy)naphthalene-2-carboxylamide, 22 mg (9.80 mmol) of palladium acetate, 0.6 ml (4.45 mmol) of methyl anthranilate and 1.45 g (4.45 mmol) of caesium carbonate are successively introduced into a solution containing 79 mg (0.13 mmol) of 2,2'-bis(diphenylphosphino)-1,1'-binaphthyl (BINAP) in 20 ml of toluene. The reaction mixture is heated at 100° C. for 8 hours and then cooled, extracted with ethyl acetate and washed with saturated sodium chloride solution. The organic phase is separated out after settling of the phases, dried over sodium sulfate, filtered and concentrated under vacuum. The residue obtained is purified by chromatography on a column of silica eluted with a heptane/ethyl acetate mixture (60/40). After evaporating off the solvents, 1.6 of methyl 2-[3'-({[6-(2-methoxyethoxymethoxy)naphthalene-2-carbonyl]-methylamino}methyl)biphenyl-4-ylamino]benzoate are obtained in the form of a pale yellow powder, in a yield of 83%.

Melting point: 80° C.

EXAMPLE 2

Synthesis of 2-[3'-({[6-(2-methoxyethoxymethoxy) naphthalene-2-carbonyl]methyl-amino}methyl)biphenyl-4-ylamino]benzoic acid 80 mg (2 mmol) of sodium hydroxide are added to a solution of 0.8 g (1.3 mmol) of methyl 2-[3'-({[6-(2-methoxyethoxymethoxy)naphthalene-2-carbonyl]methylamino}methyl)biphenyl-4-ylamino]benzoate in 8 ml of tetrahydrofuran, 0.8 ml of methanol and a few drops of water. After stirring at room temperature for 8 hours, the reaction medium is diluted with ethyl acetate, washed with aqueous 1N hydrochloric acid solution, extracted with ethyl acetate, dried over sodium sulfate, filtered and concentrated under vacuum. The residue obtained is purified by chromatography on a column of silica eluted with a 70/30 heptane/ethyl acetate mixture and then triturated from heptane. 390 mg (50%) of 2-[3'-({[6-(2-methoxyethoxymethoxy)-naphthalene-2-carbonyl]methylamino}methyl)biphenyl-4-ylamino]benzoic acid are obtained in the form of a yellow powder.

Melting point: 72° C.

EXAMPLE 3

Synthesis of N-{4'-[2-(2,5-difluorobenzylcarbamoyl)phenylamino]biphenyl-3-ylmethyl}-N-methyl-6-(2-methoxyethoxymethoxy)naphthalene-2-carboxylamide 19 mg (50.0 µmol) of O-(7-azabenzotriazol-1-yl)-N,N,N',N'-tetramethyluronium hexafluorophosphate (HATU), 49 mg (68.0 µmol) of PS-carbodiimide resin and 0.4 ml (31 µmol) of a solution of 44.3 mg of 2,5-difluorobenzylamine in 4 ml of dichloromethane are successively added to a solution containing 20 mg (33.8 µmol) of 2-[3'-({[6-(2-methoxyethoxymethoxy)naphthalene-2-carbonyl]methylamino}methyl)biphenyl-4-ylamino]benzoic acid (Example 2) in 0.4 ml of dimethylformamide. After stirring for 3 hours 30 minutes, the reaction medium is filtered and the solvents are evaporated off. The crude reaction product is dissolved in 1.5 ml of dichloromethane and 0.4 ml of dimethylformamide, and 100 mg (274 μmol) of MP-carbonate resin are added. After stirring for 5 hours, the resin is filtered off and the solvents are evaporated off. The residue obtained is purified by chromatography on a column of silica eluted with a 1/1 heptane/ethyl acetate mixture, followed by increasing the polarity to 2/3. 15.2 mg (63%) of N-{4'-[2-(2,5-difluorobenzylcarbamoyl)phenylamino]biphenyl-3-yl-methyl}-N-methyl-6-(2-methoxyethoxymethoxy)naphtha-lene-2-carboxylamide are obtained.

HPLC Hypersil Thermoquest, Hypurity Elite C18, 5 microns, 2.1×150 mm, mobile phase: A ($CH_3CN/0.1$ v/v $HCO_2H$); B ($H_2O/0.1$ v/v $HCO_2H$), flow rate: 0.5 ml/min, gradient: 0 min: 35% B, 25 min: 5% B, 30 min. 5% B, flow rate: 0.5 ml/min, retention time: 19.6 min, purity: 97%, MS (ESI) m/z 716.3 $(M+H)^+$.

EXAMPLE 4

Synthesis of N-{4'-[2-benzylmethylcarbamoyl)phe-nylamino]biphenyl-3-ylmethyl}-N-methyl-6-(2-methoxyethoxymethoxy)naphthalene-2-carboxyla-mide In a manner similar to that of Example 3, starting with 20 mg (33.8 μmol) of 2-[3'-({[6-(2-methoxyethoxymethoxy) naphthalene-2-carbonyl]methylamino}methyl)biphenyl-4-ylamino]benzoic acid (Example 2) and 0.4 ml (31 μmol) of a solution of 37.5 mg of N-methylbenzylamine in 4 ml of DCM, 13.1 mg (56%) of N-{4'-[2-benzylmethylcarbamoyl) phenyl-amino]biphenyl-3-ylmethyl}-N-methyl-6-(2-meth-oxy-ethoxymethoxy)naphthalene-2-carboxylamide are obtained.

HPLC Hypersil Thermoquest Hypurity Elite C18, 5 microns, 2.1×150 mm, mobile phase: A ($CH_3CN/0.1$ v/v $HCO_2H$); B ($H_2O/0.1$ v/v $HCO_2H$), flow rate: 0.5 ml/min, gradient: 0 min: 35% B, 25 min: 5% B, 30 min, 5% B, flow rate: 0.5 ml/min, retention time: 19.0 min, purity: 97.6%, MS (ESI) m/z 694.3 $(M+H)^+$

EXAMPLE 5

Synthesis of methyl 2-{3-[(methyloctanoylamino) methyl]biphenyl-4-ylamino}benzoate (a) Preparation of N-(4'-bromobiphenyl-3-ylmethyl)-N-methyloctanoylamide:

1.2 ml (7.0 mmol) of octanoyl chloride are added drop-wise at room temperature to a solution of 2 g (6.4 mmol) of (4'-bromobiphenyl-3-ylmethyl)methylamine hydrochloride, obtained as described in Example 1b), in 25 ml of tetrahy-drofuran and 2.7 ml (19.2 mmol) of triethylamine. After stirring for 2 hours at room temperature, the reaction medium is immersed into water and extracted with ethyl acetate. The organic phase is dried over magnesium sulfate, filtered and evaporated. The residue obtained is purified by chromatography on a column of silica eluted with an 80/20 heptane/ethyl acetate mixture. 1.7 g (66%) of N-(4'-bromo-biphenyl-3-ylmethyl)-N-methyloctanoylamide are obtained.

(b) Synthesis of methyl 2-{3'-[(methyloctanoylamino) methyl]-biphenyl-4-ylamino}benzoate:

19 mg (8.4 mmol) of palladium acetate are introduced into a solution containing 78 mg (0.13 mmol) of BINAP in 2 ml of toluene, followed by successive addition of 1.7 g (4.2 mmol) of N-(4'-bromobiphenyl-3-ylmethyl)-N-methyloc-tanoylamide, 25 ml of toluene, 0.65 ml (5 mmol) of methyl anthranilate and 0.56 g (5.9 mmol) of sodium tert-butoxide. The reaction mixture is heated at 90° C. for 24 hours. 78 mg (8.4 mmol) of tris(dibenzylideneacetone)dipalladium (0) ($Pd_2$ $dba_3$), 78 mg (0.13 mmol) of BINAP and 1.9 g (5.9 mmol) of caesium carbonate are added and the reaction medium is then heated for a further 24 hours. After cooling to room temperature, the reaction medium is extracted with ethyl acetate, washed with water and acidified to pH 6–7 with aqueous 1N hydrochloric acid solution. The organic phase is separated out after settling of the phases, dried over magnesium sulfate, filtered and concentrated under vacuum. The residue obtained is purified by chromatography on a column of silica eluted with a heptane/ethyl acetate mixture (80/20). After evaporating off the solvents, 1.0 g of methyl 2-{3'-[(methyloctanoylamino)methyl]biphenyl-4-ylamino}benzoate is obtained in the form of a yellow oil, in a yield of 50%.

$^1$H NMR (δ $CDCl_3$): 0.6 (m, 3H); 1.25–1.35 (m, 8H); 1.68 (m, 2H); 2.95 and 2.99 (2s, 3H); 3.91 (s, 3H); 4.60 and 4.66 (2s, 2H); 6.75 (m, 1H); 7.15–7.60 (m, 9H); 7.98 (d, J=9 Hz, 1H); 9.54 (m, 1H).

EXAMPLE 6

Synthesis of 2-{3'-[(methyloctanoylamino)methyl] biphenyl-4-ylamino}benzoic acid 320 mg (0.7 mmol) of methyl 2-{3[(methyl-octanoy-lamino)methyl]biphenyl-4-ylamino}benzoate obtained as described in Example 5, are placed in 5 ml of tetrahydro-furan, 1 ml of methanol and a few drops of water. 135 mg (3.4 mmol) of sodium hydroxide are added and the reaction medium is stirred at room temperature for 4 hours. The reaction medium is then extracted with ethyl acetate, acidi-fied to pH 6 with aqueous 1N hydrochloric acid solution and washed with water. The organic phase is dried over mag-nesium sulfate, filtered and evaporated. The residue obtained is purified by chromatography on a column of silica, eluted with a 70/30 heptane/ethyl acetate mixture. 200 mg of 2-{3'-[(methyloctanoylamino)methyl]biphenyl-4-ylamino}benzoic acid are obtained in a yield of 65%, in the form of a yellow solid.

$^1$H NMR (δ $CDCl_3$): 0.79 (m, 3H); 1.17–1.27 (m, 8H); 1.66 (q, J=14 Hz, 2H); 2.36 (t, J=16 Hz, 2H); 2.90 and 2.94 (2s, 3H); 4.45–4.61 (2s, 2H); 6.7 (m, 1H); 7.18–7.50 (m, 10H); 7.99 (dd, J=8 Hz and J=1.5 Hz, 1H); 9.42 (s, 1H).

Melting point: 45° C.

EXAMPLE 7

Synthesis of methyl 2-(methyl-{3'-[(methyloctanoy-lamino)methyl]biphenyl-4-yl}amino)benzoate 52 mg (1.3 mmol) of sodium hydride are added to a solution of 270 mg (0.6 mmol) of 2-{3'-[(methyloctanoy-lamino)methyl]biphenyl-4-ylamino}benzoic acid (prepared as described in Example 6) in 5 ml of dimethylformamide, followed by addition of 2.5 ml of iodomethane. After heating at 100° C. for 12 hours, the medium is cooled, immersed into water and extracted with ethyl acetate. The organic phase is dried over sodium sulfate, filtered and concentrated under vacuum. The residue obtained is purified by chromatography on a column of silica eluted with an 80/20 heptane/ethyl acetate mixture. 210 mg of methyl 2-(methyl-{3'-[(methyloctanoylamino)methyl]biphenyl-4-yl}amino)benzoate are obtained in the form of a yellow oil, in a yield of 72%.

HPLC Hypersil Thermoquest Hypurity Elite C18, 5 microns, 2.1×150 mm, mobile phase: A ($CH_3CN/0.1$ v/v HCO$_2$H); B (H$_2$O/0.1 v/v HCO$_2$H), flow rate: 0.5 ml/min, gradient: 0 min: 35% B, 25 min: 5% B, 30 min. 5% B, flow rate: 0.5 ml/min, retention time: 21.8 min, purity: 96%, MS (ESI) m/z 487.2 (M+H)$^+$

EXAMPLE 8

Synthesis of 2-(methyl-{3'-[(methyloctanoylamino) methyl]biphenyl-4-yl}amino)benzoic acid 190 mg (0.4 mmol) of methyl 2-(methyl-{3'-[(methyloctanoylamino)methyl]biphenyl-4-yl}amino)benzoate are placed in 2 ml of tetrahydrofuran, 0.2 ml of methanol and a few drops of water. 24 mg (0.6 mmol) of sodium hydroxide are added and the reaction medium is stirred at room temperature for 18 hours. The reaction medium is then extracted with ethyl acetate, acidified to pH 5 with aqueous 1N hydrochloric acid solution and washed with water. The organic phase is dried over magnesium sulfate, filtered and evaporated. The residue obtained is purified by chromatography on a column of silica eluted with an 80/20 heptane/ ethyl acetate mixture.

155 mg of 2-(methyl-{3'-[(methyloctanoylamino)methyl] biphenyl-4-yl}amino)benzoic acid are obtained in the form of a yellow oil in a yield of 84%.

HPLC Hypersil Thermoquest Hypurity Elite C18, 5 microns, 2.1×150 mm, mobile phase: A (CH$_3$CN/0.1 v/v HCO$_2$H); B (H$_2$O/0.1 v/v HCO$_2$H), flow rate: 0.5 ml/min, gradient: 0 min: 35% B, 25 min: 5% B, 30 min. 5% B, flow rate: 0.5 ml/min, retention time: 18.8 min, purity: 97%, MS (ESI) m/z 473.4 (M+H)$^+$

EXAMPLE 9

Synthesis of N-(3-methylbutyl)-2-{3'-[(methyloctanoylamino)methyl]biphenyl-4-ylamino}benzamide 95 mg (1.1 mmol) of 3-methylbutylamine and 160 mg (1.2 mmol) of 1-hydroxybenzotriazole are successively added to a solution of 500 mg (1.1 mmol) of 2-{3'-[(methyloctanoylamino)methyl]biphenyl-4-ylamino}benzoic acid (Example 6) in 15 ml of dichloromethane. The reaction medium is cooled to 0° C. and 230 mg (1.2 mmol) of EDCl are added portionwise. The reaction medium is stirred from 0° C. to room temperature over 6 hours, diluted with ethyl acetate, washed with water and extracted with ethyl acetate. The organic phase is dried over sodium sulfate, filtered and evaporated. The residue obtained is purified by chromatography on a column of silica eluted with an 80/20 heptane/ ethyl acetate mixture. 530 mg of N-(3-methylbutyl)-2-{3'-[(methyloctanoylamino)methyl]biphenyl-4-ylamino}benzamide are obtained in the form of a yellow oil, in a yield of 93%.

HPLC Hypersil Thermoquest Hypurity Elite C18, 5 microns, 2.1×150 mm, mobile phase: A (CH$_3$CN/0.1 v/v HCO$_2$H); B (H$_2$O/0.1 v/v HCO$_2$H), flow rate: 0.5 ml/min, gradient: 0 min: 35% B, 25 min: 5% B, 30 min. 5% B, flow rate: 0.5 ml/min, retention time: 22.8 min, purity: 99%, MS (ESI) m/z 526.3 (M+H)$^+$

EXAMPLE 10

Synthesis of N-methyl-N-{4'-[2-(5-propyl-[1,3,4] oxadiazol-2-yl)phenylamino]biphenyl-3-ylmethyl}octanoylamide (a) Preparation of N-methyl-N-[4'-(2-hydrazinocarbonylphenyl-amino)biphenyl-3-ylmethyl]octanoylamide:

0.16 ml (1.4 mmol) of 4-methylmorpholine and 0.2 ml (1.5 mmol) of isobutyl chloroformate are successively added to a solution of 500 mg (1.1 mmol) of 2-{3'-[(methyloctanoylamino)methyl]biphenyl-4-ylamino}benzoic acid (Example 6) in 15 ml of tetrahydrofuran, cooled to 0° C. The reaction medium is stirred at room temperature for 1 hour. The precipitate is filtered off and the filtrate is collected into 5.5 ml of a 1M solution of hydrazine in tetrahydrofuran, cooled to 0° C. After stirring from 0° C. to room temperature over 1 hour, the reaction medium is diluted with ethyl acetate and washed with saturated ammonium chloride solution and then with sodium chloride. The organic phase is dried over sodium sulfate, filtered and concentrated under vacuum. The residue obtained is purified by chromatography on a column of silica eluted with a 60/40 heptane/ethyl acetate mixture. 390 mg of N-methyl-N-[4'-(2-hydrazinocarbonylphenylamino)biphenyl-3-ylmethyl]octanoylamide are obtained in a yield of 52%.

(b) Synthesis of N-methyl-N-{4'-[2-(5-propyl-[1,3,4]oxadiazol-2-yl)phenylamino]biphenyl-3-ylmethyl}octanoylamide:

0.36 ml (2.2 mmol) of trimethyl orthobutyrate and 9.6 µl (0.15 mmol) of methanesulfonic acid are added to a solution of 350 mg (0.74 mmol) of N-methyl-N-[4'-(2-hydrazinocarbonylphenylamino)biphenyl-3-ylmethyl]octanoylamide in 10 ml of dioxane, and the mixture is then heated at 105° C. for 1 hour. After cooling, the medium is diluted with ethyl acetate and then washed with saturated sodium hydrogen carbonate solution and then with sodium chloride solution. The organic phase is dried over sodium sulfate, filtered and concentrated. The residue obtained is purified by chromatography on a column of silica eluted with a 70/30 heptane/ ethyl acetate mixture. 270 mg of N-methyl-N-{4'-[2-(5-propyl-[1,3,4]oxadiazol-2-yl)phenylamino]biphenyl-3-ylmethyl}octanoylamide are obtained in the form of an orange-colored oil, in a yield of 70%.

HPLC Hypersil Thermoquest Hypurity Elite C18, 5 microns, 2.1×150 mm, mobile phase: A (CH$_3$CN/0.1 v/v HCO$_2$H); B (H$_2$O/0.1 v/v HCO$_2$H), flow rate: 0.5 ml/min, gradient: 0 min: 35% B, 25 min: 5% B, 30 min. 5% B, flow rate: 0.5 ml/min, retention time: 23.9 min, purity: 97%, MS (ESI) m/z 525.4 (M+H)$^+$

EXAMPLE 11

Synthesis of N-methyl-N-{4'-[2-(1H-tetrazol-5-yl) phenylamino]biphenyl-3-ylmethyl}octanoylamide (a) Preparation of N-methyl-N-[4'-(2-cyanophenylamino) biphenyl-3-ylmethyl]octanoylamide:

In a manner similar to that of Example 1(e), starting with 1.0 g (2.5 mmol) of N-(4'-bromobiphenyl-3-ylmethyl)-N-methyloctanoylamide, obtained as in Example 5(a), and 0.4 g (3.5 mmol) of anthranilonitrile, 1.0 g of N-methyl-N-[4'-(2-cyanophenylamino)biphenyl-3-ylmethyl]octanoylamide is obtained in a yield of 96%.

(b) Synthesis of N-methyl-N-{4'-[2-(1H-tetrazol-5-yl) phenylamino]biphenyl-3-ylmethyl}octanoylamide:

230 mg (1.7 mmol) of triethylamine hydrochloride and 220 mg (3.4 mmol) of sodium azide are added to a solution of 500 mg (1.14 mmol) of N-methyl-N-(4'-(2-cyanophenylamino)biphenyl-ylmethyl]octanoylamide in 5 ml of 1-methyl-2-pyrrolidinone. The reaction medium is heated at 150° C. for 4 hours. After cooling, aqueous 1N hydrochloric acid solution is added to the reaction medium to pH 4, followed by extraction with ethyl acetate. The organic phase is dried over sodium sulfate, filtered and concentrated. The residue obtained is purified by chromatography on a column of silica eluted with a 95/5 dichloromethane/methanol mixture. 369 mg of N-methyl-N-{4'-[2-(1H-tetrazol-5-yl)phenylamino]biphenyl-3-ylmethyl}octanoylamide are obtained in the form of a yellow oil, in a yield of 68%.

HPLC Hypersil Thermoquest Hypurity Elite C18, 5 microns, 2.1×150 mm, mobile phase: A (CH$_3$CN/0.1 v/v HCO$_2$H); B (H$_2$O/0.1 v/v HCO$_2$H), flow rate: 0.5 ml/min, gradient: 0 min: 35% B, 25 min: 5% B, 30 min. 5% B, flow rate: 0.5 ml/min, retention time: 19.6 min, purity: 96%, MS (ESI) m/z 483.3 (M+H)$^+$

EXAMPLE 12

Synthesis of ethyl 3-[3'-({[6-(2-methoxy-ethoxymethoxy)naphthalene-2-carbonyl]methylamino}methyl)biphenyl-4-ylamino]benzoate In a manner similar to that of Example 1(e), starting with 5.9 g (11 mmol) of N-(4'-bromobiphenyl-3-ylmethyl)-N-methyl-6-(2-methoxyethoxymethoxy)naphthalene-2-carboxylamide, prepared as described in Example 1(d), and 2.5 g (15.4 mmol) of ethyl 3-aminobenzoate, 6.8 g of ethyl 3-[3''-({[6-(2-methoxyethoxymethoxy)naphthalene-2-carbonyl]methylamino}methyl)biphenyl-4-ylamino]benzoate are obtained in the form of a beige-colored solid, in a yield of 90%.

Melting point: 85–86° C.

EXAMPLE 13

Synthesis of 3-[3'-({[6-(2-methoxyethoxymethoxy)naphthalene-2-carbonyl]methyl-amino}methyl)biphenyl-4-ylamino]benzoic acid 1.2 ml (1.2 mmol) of aqueous 1M lithium hydroxide solution are added to a solution of 500 mg (0.8 mmol) of ethyl 3-[3'-({[6-(2-methoxyethoxymethoxy)naphthalene-2-carbonyl]methylamino}methyl)-biphenyl-4-ylamino]benzoate in 10 ml of tetrahydrofuran and 1 ml of methanol. After heating at 50° C. for 18 hours, the reaction medium is diluted with ethyl acetate, washed with aqueous 1N hydrochloric acid solution, extracted with ethyl acetate, dried over magnesium sulfate, filtered and concentrated under vacuum. The residue obtained is purified by chromatography on a column of silica eluted with a 60/40 heptane/ethyl acetate mixture. 480 mg of 3-[3'-({[6-(2-methoxyethoxymethoxy)naphthalene-2-carbonyl]-methylamino}methyl)biphenyl-4-ylamino]benzoic acid are obtained in the form of a yellow foam, in a yield of 60%.

Melting point: 60° C.

EXAMPLE 14

Synthesis of ethyl 3-(3'-{[(6-hydroxynaphthalene-2-carbonyl)methylamino]methyl}biphenyl-4-ylaminobenzoate 1 ml of concentrated sulfuric acid is added to a solution of 1.2 g (1.9 mmol) of ethyl 3-[3'-({[6-(2-methoxy-ethoxymethoxy)naphthalene-2-carbonyl]methylamino}methyl)biphenyl-4-ylamino]benzoate in 10 ml of methanol and 10 ml of tetrahydrofuran. The reaction medium is stirred at room temperature for 6 hours, diluted with ethyl acetate and washed with water. After extraction, the organic phase is dried over magnesium sulfate, filtered and concentrated under vacuum. The residue obtained is purified by chromatography on a column of silica eluted with a 60/40 heptane/ethyl acetate mixture. 1 g of ethyl 3-(3'-{[(6-hydroxynaphthalene-2-carbonyl) methylamino]methyl}biphenyl-4-ylamino)benzoate is obtained in the form of a beige-colored foam, in a yield of 80%.

Melting point: 90° C.

EXAMPLE 15

Synthesis of 3-(3'-{[(6-hydroxynaphthalene-2-carbonyl)methylamino]methyl}biphenyl-4-ylamino) benzoic acid In a manner similar to that of Example 13, starting with 820 mg (1.5 mmol) of ethyl 3-(3'-{[(6-hydroxynaphthalene-2-carbonyl)methylamino]methyl}biphenyl-4-ylamino)benzoate and 4.3 ml (4.3 mmol) of aqueous 1M lithium hydroxide solution, 770 mg of 3-(3'-{[(6-hydroxynaphthalene-2-carbonyl)methylamino]methyl}biphenyl-4-ylamino) benzoic acid are obtained in the form of a yellow foam, in a yield of 78%.

Melting point: 105° C.

EXAMPLE 16

Synthesis of N-methyl-N-{4'-[3-(4-methylpiperidine-1-carbonyl)phenylamino]biphenyl-3-ylmethyl}-6-(2-methoxyethoxymethoxy)naphthalene-2-carboxylamide 0.18 ml (1.3 mmol) of triethylamine, 170 mg (1.3 mmol) of 1-hydroxybenzotriazole and 0.14 ml (1.2 mmol) of 4-methylpiperidine are successively added to a solution of 700 mg (1.2 mmol) of 3-[3'-({[6-(2-methoxyethoxymethoxy)naphthalene-2-carbonyl]methyl-amino}methyl)biphenyl-4-ylamino]benzoic acid in 15 ml of dichloromethane. The reaction medium is cooled to 0° C. and 250 mg (1.3 mmol) of EDCl are then added. After stirring from 0° C. to room temperature over 6 hours, the reaction medium is washed with water and extracted with dichloromethane. The organic phase is dried over magnesium sulfate, filtered and concentrated under vacuum. The residue obtained is purified by chromatography on a column of silica eluted with a 50/50 heptane/ethyl acetate mixture. 810 mg of N-methyl-N-{4'-[3-(4-methylpiperidine-1-carbonyl) phenylamino]biphenyl-3-ylmethyl}6-(2-methoxyethoxy-methoxy)naphthalene-2-carboxylamide are obtained in the form of a yellow solid, in a yield of 62%.

Melting point: 60° C.

EXAMPLE 17

Synthesis of N-methyl-N-{4'-[3-(morpholine-3-carbonyl)phenylamino]biphenyl-3-ylmethyl}-6-(2-methoxyethoxy-methoxy)naphthalene-2-carboxylamide In a manner similar to that of Example 16, starting with 650 mg (1.1 mmol) of 3-[3'-({[6-(2-methoxy-ethoxymethoxy)naphthalene-2-carbonyl]methylamino}methyl)biphenyl-4-ylamino]benzoic acid and 0.1 ml (1.1 mmol) of morpholine, 720 mg of N-methyl-N-{4'-[3-(morpholine-4-carbonyl)phenylamino]biphenyl-3-ylmethyl}-6-(2-methoxyethoxy-methoxy)naphthalene-2-carboxylamide are obtained in the form of a white foam, in a yield of 69%.

Melting point: 68–70° C.

EXAMPLE 18

Synthesis of N-methyl-N-{4'-[3-(4-methylpiperidine-1-carbonyl)phenylamino]biphenyl-3-ylmethyl}-6-hydroxynaphthalene-2-carboxylamide In a manner similar to that of Example 14, starting with 150 mg (0.22 mmol) of N-methyl-N-{4'-[3-(4-methylpiperidine-1-carbonyl)phenylamino]biphenyl-3-ylmethyl}-6-(2-methoxyethoxymethoxy)naphthalene-2-carboxylamide, 130 mg of N-methyl-N-{4'-[3-(4-methylpiperidine-1-carbonyl) phenylamino]biphenyl-3-ylmethyl}-6-hydroxynaphthalene-2-carboxylamide are obtained in the form of a white solid, in a yield of 100%.

Melting point: 90° C.

EXAMPLE 19

Synthesis of N-methyl-N-{4'-[3-(morpholine-4-carbonyl)phenylamino]biphenyl-3-ylmethyl}-6-hydroxynaphthalene-2-carboxylamide In a manner similar to that of Example 14, starting with 160 mg (0.24 mmol) of N-methyl-N-{4'-[3-(morpholine-4-carbonyl)phenylamino]biphenyl-3-ylmethyl}-6-(2-methoxyethoxymethoxy)naphthalene-2-carboxylamide, 120 mg of N-methyl-N-{4'-[3-morpholine-4-carbonyl)phenylamino]biphenyl-3-ylmethyl}-6-hydroxynaphthalene-2-carboxylamide are obtained in the form of a white solid, in a yield of 86%.

Melting point: 92° C.

EXAMPLE 20

Synthesis of 3-{3'-[(methyloctanoylamino)methyl] biphenyl-4-ylamino}benzoic acid (a) Preparation of ethyl 3-{3'-[(methyloctanoylamino)methyl]biphenyl-4-ylamino}benzoate:

In a manner similar to that of Example 1(e), starting with 500 mg (1.24 mmol) of N-(4'-bromobiphenyl-3-ylmethyl)-N-methyloctanoylamide, prepared as described in Example 5(a) and 0.26 ml (1.74 mmol) of ethyl 3-aminobenzoate, 570 mg of ethyl 3-{3'-[(methyl-octanoylamino)methyl]biphenyl-4-ylamino}benzoate are obtained in the form of a yellow oil, in a yield of 95%.

(b) Synthesis of 3-{3'-[(methyloctanoylamino)methyl]biphenyl-4-ylamino}benzoic acid:

In a manner similar to that of Example 2, starting with 500 mg (1 mmol) of ethyl 3-{3'-[(methyloctanoylamino)methyl] biphenyl-4-ylamino}benzoate, 390 mg of 3-{3'-[(methyloctanoylamino)methyl]biphenyl-4-ylamino}benzoic acid are obtained in the form of a yellow foam, in a yield of 83%.

Melting point: 58° C.

EXAMPLE 21

Synthesis of ethyl 2-{3'-[(Methyloctanoylamino) methyl]biphenyl-4-yloxy}benzoate (a) Preparation of tert-butyl (3-bromobenzyl)carbamate:

40 g (183 mmol) of di-tert-butyl dicarbonate are added portionwise, at room temperature, to a mixture of 40.7 g (183 mmol) of 3-bromobenzylamine hydrochloride, 26 ml of triethylamine (183 mmol) and 450 ml of dichloromethane. After stirring for 18 hours, the reaction medium is poured into ice-cold water and extracted with dichloromethane. The organic phase is separated out after settling of the phases, dried over magnesium sulfate and evaporated. 46 g of tert-butyl (3-bromobenzyl)carbamate are obtained in a yield of 88%.

(b) Preparation of tert-butyl (3-bromobenzyl)-N-methylcarbamate:

19 g (475 mmol) of sodium hydride (60% in oil) are added portionwise to a solution of 128 g (447 mmol) of tert-butyl (3-bromobenzyl)carbamate in 800 ml of DMF, and the reaction medium is stirred until the evolution of gas has ceased. 29.3 ml (470 mmol) of methyl iodide are added dropwise and stirring is continued for 18 hours. The reaction medium is poured into ice-cold water and extracted with ethyl acetate. The organic phase is separated out after settling has taken place, dried over magnesium sulfate and evaporated. 152.5 g of tert-butyl (3-bromobenzyl)-N-methylcarbamate are obtained in a yield of 92%.

(c) Preparation of tert-butyl (4'-hydroxybiphenyl-3-ylmethyl)methylcarbamate:

41.6 ml (83.2 mmol) of aqueous 2M potassium carbonate solution are added dropwise to a solution of 10 g (33 mmol) of tert-butyl (3-bromobenzyl)-N-methylcarbamate and 8.3 g (60 mmol) of 4-hydroxy-benzeneboronic acid in 100 ml of ethylene glycol dimethyl ether. The reaction medium is degassed and 1.9 g (1.7 mmol) of tetrakis(triphenylphosphino)palladium are added. After heating for 12 hours at 80° C., the reaction medium is cooled, diluted with water and extracted with ethyl acetate. The organic phase is dried over sodium sulfate, filtered and concentrated under vacuum. The residue obtained is purified by chromatography on a column of silica eluted with an 80/20 heptane/ethyl acetate mixture. 7 g of tert-butyl (4'-hydroxybiphenyl-3-ylmethyl)methylcarbamate are obtained in the form of a beige-colored solid, in a yield of 68%.

Melting point: 174° C.

(d) Preparation of ethyl 2-{3'-[(tert-butoxycarbonylmethylamino)methyl]biphenyl-4-yloxy}benzoate:

2.15 g (12.8 mmol) of ethyl 2-fluorobenzoate and 1.9 g (14 mmol) of potassium carbonate are successively added to a solution of 4 g (12.8 mmol) of tert-butyl(4'-hydroxybiphenyl-3-ylmethyl)methylcarbamate in 45 ml of dimethylacetamide. The reaction medium is refluxed for 48 hours, cooled, diluted with water and extracted with ethyl acetate. The organic phase is dried over sodium sulfate, filtered and concentrated under vacuum. The residue obtained is purified by chromatography on a column of silica eluted with an 80/20 heptane/ethyl acetate mixture. 3.1 g of ethyl 2-{3'-[(tert-butoxycarbonylmethylamino)methyl]biphenyl-4-yloxy}benzoate are obtained in the form of a colorless oil, in a yield of 53%.

(e) Preparation of ethyl 2-(3'-methylaminomethylbiphenyl-4-yloxy)benzoate:

3.1 g (6.7 mmol) of ethyl 2-{3'-[(tert-butoxycarbonylmethylamino)-methyl]biphenyl-4-yloxy}benzoate are placed in 50 ml of dichloromethane and 2.6 ml of trifluoroacetic acid. After stirring at room temperature for 8 hours, the reaction medium is concentrated, placed in water, brought to pH 8 with aqueous 1N sodium hydroxide solution and extracted with ethyl acetate. The organic phase is dried over sodium sulfate, filtered and concentrated under vacuum. 2.3 g of ethyl 2-(3'-methylaminomethylbiphenyl-4-yloxy)benzoate are obtained in the form of an orange-colored oil, in a yield of 95%.

(f) Synthesis of ethyl 2-{3'-[(methyloctanoylamino)methyl]biphenyl-4-yloxy}benzoate:

In a manner similar to that of Example 5(a), starting with 2.3 g (6.4 mmol) of ethyl 2-(3'-methylaminomethylbiphenyl-4-yloxy)benzoate and 1.1 ml (6.4 mmol) of octanoyl chloride, 2.9 g of ethyl 2-{3'-[(methyloctanoylamino)methyl]biphenyl-4-yloxy}benzoate are obtained in the form of a colorless oil, in a yield of 92%.

HPLC Hypersil Thermoquest Hypurity Elite C18, 5 microns, 2.1×150 mm, mobile phase: A (CH$_3$CN/0.1 v/v HCO$_2$H); B (H$_2$O/0.1 v/v HCO$_2$H), flow rate: 0.5 ml/min, gradient: 0 min: 35% B, 25 min: 5% B, 30 min. 5% B, flow rate: 0.5 ml/min, retention time: 21.5 min, purity: 99%, MS (ESI) m/z 488.3 (M+H)$^+$

EXAMPLE 22

Synthesis of 2-{3'-[methyloctanoylamino)methyl] biphenyl-4-yloxy}benzoic acid

In a manner similar to that of Example 8, starting with 1 g (2 mmol) of ethyl 2-{3'-[(methyloctanoylamino)methyl]biphenyl-4-yloxy}benzoate, 800 mg of 2-{3'-[methyloctanoylamino)methyl]biphenyl-4-yloxy}benzoic acid are obtained in the form of a white solid, in a yield of 85%.

Melting point: 115° C.

EXAMPLE 23

Crossover-curve PPAR Transactivation Test

The activation of receptors with an agonist (activator) in HeLN cells leads to the expression of a reporter gene, luciferase, which, in the presence of a substrate, generates light. The modulation of the receptors is measured by quantifying the luminescence produced after incubating the cells in the presence of a reference agonist. The ligands displace the agonist from its site. The measurement of the activity is performed by quantifying the light produced. This measurement makes it possible to determine the modulatory activity of the compounds according to the invention by determining the constant that is the affinity of the molecule for the receptor. Since this value can fluctuate depending on the basal activity and the expression of the receptor, it is referred to as Kd apparent (KdApp in nM).

To determine this constant, "crossover curves" of the test product against a reference agonist are performed in a 96-well plate: 10 concentrations of the test product plus a concentration 0 are arranged in a line, and 7 concentrations of the agonist plus a concentration 0 are arranged in a column. This is 88 measurement points for 1 product and 1 receptor. The remaining 8 wells are used for repeatability controls.

In each well, the cells are in contact with a concentration of the test product and a concentration of the reference agonist, 2-(4-{2-[3-(2,4-difluoro-phenyl)-1-heptylureido]ethyl}phenylsulfanyl)-2-methylpropionic acid for PPARα, {2-methyl-4-[4-methyl-2-(4-trifluoromethylphenyl)thiazol-5-ylmethylsulfanyl]phenoxy}acetic acid for PPARδ and 5-{4-[2-(methylpyrid-2-ylamino)ethoxy]benzyl}thiazolidine-2,4-dione for PPARγ. Measurements are also taken for total agonist controls with the same products.

The HeLN cell lines used are stable transfectants containing the plasmids ERE-βGlob-Luc-SV-Neo (reporter gene) and PPAR (α, δ, γ) Gal-hPPAR. These cells are inoculated into 96-well plates at a rate of 10 000 cells per well in 100 μl of DMEM medium without phenol red and supplemented with 10% of defatted calf serum. The plates are then incubated at 37° C. and 7% CO$_2$ for 16 hours.

The various dilutions of the test products and of the reference ligand are added at a rate of 5 μl per well. The plates are then incubated for 18 hours at 37° C. and 7% CO$_2$. The culture medium is removed by turning over and 100 μl of a 1:1 PBS/luciferine mixture are added to each well. After 5 minutes, the plates are read by the luminescence detector.

These crossed curves make it possible to determine the AC50 values (concentration at which 50% activation is observed) of the reference ligand at various concentrations of test product. These AC50 values are used to calculate the Schild regression by plotting a straight line corresponding to the Schild equation ("quantitation in receptor pharmacology" Terry P. Kenakin, *Receptors and Channels,* 2001, 7, 371–385) which allows the Kd app values (in nM) to be obtained.

Transactivation results:

| Compounds | PPARα Kd app (nM) | PPARδ Kd app (in nM) | PPARγ Kd app (in nM) |
|---|---|---|---|
| Reference 1: 2-(4-{2-[3-(2,4-difluorophenyl)-1-heptylureido]-ethyl}phenylsulfanyl)-2-methyl-propionic acid | 200 | n.a. | n.a. |
| Reference 2: {2-methyl-4-[4-methyl-2-(4-trifluoromethylphenyl)thiazol-5-ylmethylsulfanyl]phenoxy}acetic acid | n.a. | 10 | n.a. |
| Reference 3: 5-{4-[2-(methylpyrid-2-ylamino)ethoxy]benzyl}thiazolidine-2,4-dione | n.a. | n.a. | 30 |
| Example 2 | n.a. | n.a. | 30 |
| Example 8 | n.a. | n.a. | 250 |
| Example 16 | n.a. | n.a. | 120 |
| Example 17 | n.a. | n.a. | 500 | n.a. means not active

These results show the affinity of the compounds for PPAR-γ and more particularly the specificity of the affinity of the compounds of the invention for the PPARγ subtype, compared with the affinity of the compounds for the PPARα subtype or for the PPARδ subtype.

EXAMPLE 24

Compositions

Various specific formulations based on the compounds according to the invention are illustrated in this example.

| A ORAL ROUTE: | |
|---|---|
| (a) 0.2 g tablet: | |
| Compound of Example 2 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |
| (b) Drinkable suspension in 5 ml ampules: | |
| Compound of Example 7 | 0.001 g |
| Glycerol | 0.500 g |
| 70% Sorbitol | 0.500 g |
| Sodium saccharinate | 0.010 g |

-continued

A ORAL ROUTE:

| | | |
|---|---|---|
| Methyl para-hydroxybenzoate | | 0.040 g |
| Flavoring | qs | |
| Purified water | qs | 5 ml |
| (c) 0.8 g tablet: | | |
| Compound of Example 1 | | 0.500 g |
| Pregelatinized starch | | 0.100 g |
| Microcrystalline cellulose | | 0.115 g |
| Lactose | | 0.075 g |
| Magnesium stearate | | 0.010 g |
| (d) Drinkable suspension in 10 ml ampules: | | |
| Compound of Example 1 | | 0.200 g |
| Glycerol | | 1.000 g |
| 70% Sorbitol | | 1.000 g |
| Sodium saccharinate | | 0.010 g |
| Methyl para-hydroxybenzoate | | 0.080 g |
| Flavoring | qs | |
| Purified | qs | 10 ml |

B TOPICAL ROUTE:

| | | |
|---|---|---|
| (a) Ointment: | | |
| Compound of Example 1 | | 0.020 g |
| Isopropyl myristate | | 81.700 g |
| Liquid petroleum jelly fluid | | 9.100 g |
| Silica ("Aerosil 200" sold by Degussa) | | 9.180 g |
| (b) Ointment: | | |
| Compound of Example 2 | | 0.300 g |
| White petroleum jelly | qs | 100 g |
| (c) Nonionic water-in-oil cream: | | |
| Compound of Example 10 | | 0.100 g |
| Mixture of emulsifying lanolin alcohols, waxes and oils ("Anhydrous Eucerin" sold by BDF) | | 39.900 g |
| Methyl para-hydroxybenzoate | | 0.075 g |
| Propyl para-hydroxybenzoate | | 0.075 g |
| Sterile demineralized water | qs | 100 g |
| (d) Lotion: | | |
| Compound of Example 9 | | 0.100 g |
| Polyethylene glycol (PEG 400) | | 69.900 g |
| 95% Ethanol | | 30.000 g |
| (e) Hydrophobic ointment: | | |
| Compound of Example 13 | | 0.300 g |
| Isopropyl myristate | | 36.400 g |
| Silicone oil ("Rhodorsil 47 V 300" sold by Rhone-Poulenc) | | 36.400 g |
| Beeswax | | 13.600 g |
| Silicone oil ("Abil 300,000 cst" sold by Goldschmidt) | qs | 100 g |
| (f) Nonionic oil-in-water cream: | | |
| Compound of Example 17 | | 1.000 g |
| Cetyl alcohol | | 4.000 g |
| Glyceryl monostearate | | 2.500 g |
| PEG-50 stearate | | 2.500 g |
| Karite butter | | 9.200 g |
| Propylene glycol | | 2.000 g |
| Methyl para-hydroxybenzoate | | 0.075 g |
| Propyl para-hydroxybenzoate | | 0.075 g |
| Sterile demineralized water | qs | 100 g |

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A polycyclic compound having the structural formula (I):

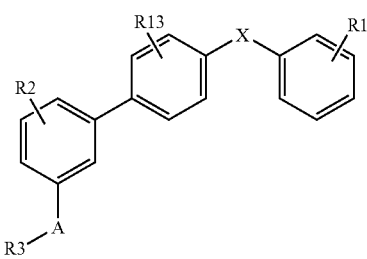

in which $R_1$ is a radical selected from among those of the following formulae (a)–(c):

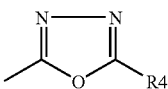

(a)

(b)

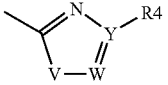

(c)

wherein $R_4$, $R_5$, V, W and Y are as defined below;

$R_2$ is a hydrogen atom, a halogen atom, an alkyl radical having from 1 to 12 carbon atoms, a hydroxyl radical, an alkoxy radical having from 1 to 7 carbon atoms, a polyether radical, a nitro radical, or an amino radical that may optionally be substituted with one or more alkyl radicals having from 1 to 12 carbon atoms, an aryl radical, an aralkyl radical, a heteroaryl radical or a heterocyclic radical; $R_3$ is a radical $-(CH_2)_t-(N-R_{15})_u-(C(O,N))_z R_{16}$, an alkyl radical having from 1 to 12 carbon atoms, an aryl radical, an aralkyl radical, a heteroaryl radical, a heterocyclic radical or a 9-fluorenylmethyl radical, wherein t, u, z, $R_{15}$ and $R_{16}$ are as defined below; $R_4$ is a hydrogen atom, an alkyl radical having from 1 to 12 carbon atoms, an aryl radical, an aralkyl radical, a heteroaryl radical or a heterocyclic radical; $R_5$ is a radical $O-(CH_2)_n-R_6$, a radical $NR'-(CH_2)_n-R_{14}$, a hydroxyl radical, an alkoxy radical having from 1 to 7 carbon atoms, an aryl radical, an aralkyl radical, a heteroaryl radical or a heterocyclic radical, or a radical:

wherein $R_6$, $R_{14}$, R', R" and n are as defined below; R' is a hydrogen atom, an alkyl radical having from 1 to 12 carbon atoms, a hydroxyl radical, an aryl radical, an aralkyl radical, a heteroaryl radical or a heterocyclic radical; R" is a hydrogen atom, an alkyl radical having from 1 to 12 carbon atoms, an aryl radical, an aralkyl radical, a heteroaryl radical, a heterocyclic radical or a radical —$(CH_2)_n$—$R_6$, wherein $R_6$ and n are as defined below; $R_6$ is an aryl radical, an aralkyl radical, a heteroaryl radical, a heterocyclic radical, a radical NH—CO—$R_7$, a radical NH—CO—O—$R_7$ or a radical N—$R_7R_8$, wherein $R_7$ and $R_8$ are as defined below; n has the values 1, 2 or 3; $R_7$ is a hydrogen atom, an alkyl radical having from 1 to 12 carbon atoms, an aryl radical, an aralkyl radical, a heteroaryl radical or a heterocyclic radical; $R_8$ is a hydrogen atom or an alkyl radical having from 1 to 3 carbon atoms; X is an oxygen or sulfur atom, or a methylene ($CH_2$) or $NR_9$ radical, wherein $R_9$ is a hydrogen atom, an alkyl radical having from 1 to 12 carbon atoms or an aralkyl radical;

A is a linking radical having the following structure:

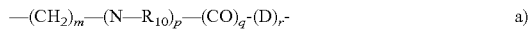

a)

or

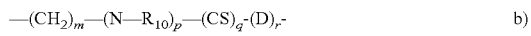

b)

wherein D, r, g, p and m are as defined below and $R_{10}$ is also as defined below; D is an oxygen or sulfur atom, a radical $NR_{11}$, or a $CH_2$ radical, wherein $R_{11}$ is as defined below; m, p, q and r, which may be identical or different, each has the values 0 or 1; $R_{10}$ and $R_{11}$, which may be identical or different, are each a hydrogen atom or an alkyl radical having from 1 to 12 carbon atoms; V is an oxygen, sulfur or nitrogen atom, the nitrogen atom being bonded to a hydrogen atom or an alkyl radical having from 1 to 6 carbon atoms; W is a nitrogen atom or a radical C—$R_{12}$, wherein $R_{12}$ is as defined below; Y is a nitrogen atom or a carbon atom; $R_{12}$ is a hydrogen atom, an alkyl radical having from 1 to 12 carbon atoms, an aryl radical, an aralkyl radical, a heteroaryl radical or a heterocyclic radical; $R_{13}$ is a hydrogen or halogen atom; $R_{14}$ is a heterocyclic radical; $R_{15}$ is a hydrogen atom, an alkyl radical having from 1 to 12 carbon atoms, an aryl radical, an aralkyl radical, a heteroaryl radical or a heterocyclic radical; t, u and z, which may be identical or different, each has a value from 0 to 4; $R_{16}$ is a hydrogen atom, an alkyl radical having from 1 to 12 carbon atoms, an aryl radical, an aralkyl radical, a heteroaryl radical, a heterocyclic radical, a radical $NHCOR_7$, a radical $NHCOOR_7$ or a radical $NR_7R_8$, wherein $R_7$ and $R_8$ are as defined above, with the proviso that, when m is 0, then q is 1 and $R_{10}$ is an alkyl radical having from 1 to 12 carbon atoms; and the optical and geometrical isomers and salts thereof.

2. The polycyclic compound as defined by claim 1, wherein formula (I), $R_1$ is a radical (a).

3. The polycyclic compound as defined by claim 1, wherein formula (I), $R_1$ is a radical (b).

4. The polycyclic compound as defined by claim 1, wherein formula (I), $R_1$ is a radical (c).

5. The polycyclic compound as defined by claim 1, wherein formula (I), A is the linking radical a).

6. The polycyclic compound as defined by claim 1, wherein formula (I), A is the linking radical b).

7. The polycyclic compound as defined by claim 1, wherein formula (I), X is an oxygen or sulfur atom.

8. The polycyclic compound as defined by claim 1, wherein formula (I), X is a methylene radical.

9. The polycyclic compound as defined by claim 1, wherein formula (I), X is a $NR_9$ radical.

10. An alkali metal or alkaline-earth metal, zinc or organic amine salt of the polycyclic compound as defined by claim 1.

11. The polycyclic compound as defined by claim 1, bearing at least one substituent selected from the group consisting of methyl, ethyl and propyl radicals.

12. The polycyclic compound as defined by claim 1, bearing at least one substituent selected from the group consisting of isopropyl, butyl, tert-butyl, hexyl, heptyl, octyl, decyl and cyclohexyl radicals.

13. The polycyclic compound as defined by claim 1, bearing at least one substituent selected from the group consisting of methoxymethoxy, ethoxymethoxy and methoxyethoxymethoxy radicals.

14. The polycyclic compound as defined by claim 1, bearing at least one substituent selected from the group consisting of fluorine, chlorine and bromine atoms.

15. The polycyclic compound as defined by claim 1, bearing at least one substituent selected from the group consisting of methoxy, ethoxy, isopropyloxy, tert-butoxy, hexyloxy, benzyloxy and phenoxy radicals, which may optionally be substituted with an alkyl radical having from 1 to 12 carbon atoms.

16. The polycyclic compound as defined by claim 1, bearing at least one substituent selected from the group consisting of phenyl, biphenyl, cinnamyl and naphthyl radicals, which may be mono- or disubstituted with a halogen atom, a $CF_3$ radical, an alkyl radical having from 1 to 12 carbon atoms, an alkoxy radical having from 1 to 7 carbon atoms, an aralkoxy radical or an aryloxy radical, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

17. The polycyclic compound as defined by claim 1, bearing at least one substituent selected from the group consisting of benzyl, phenethyl and 2-naphthylmethyl radicals, which may be mono- or disubstituted with a halogen atom, a $CF_3$ radical, an alkyl radical having from 1 to 12 carbon atoms, an alkoxy radical having from 1 to 7 carbon atoms, an aralkoxy radical or an aryloxy radical, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

18. The polycyclic compound as defined by claim 1, bearing at least one substituent selected from the group consisting of pyridyl, furyl, thienyl, isoxazolyl, oxadiazolyl, oxazolyl, benzimidazolyl, indolyl and benzofuran radicals, optionally substituted with at least one halogen, an alkyl radical having from 1 to 12 carbon atoms, an alkoxy radical having from 1 to 7 carbon atoms, an aralkoxy radical or an aryloxy radical, an aryl radical, a nitro function, a polyether radical, an aryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl radical having from 1 to 12 carbon atoms.

19. The polycyclic compound as defined by claim 1, bearing at least one substituent selected from the group consisting of morpholino, piperidino, piperazino, 2-oxo-1-piperidyl and 2-oxo-1-pyrrolidinyl radicals, optionally substituted with at least one alkyl radical having from 1 to 12 carbon atoms, an alkoxy radical having from 1 to 7 carbon atoms, an aralkoxy radical or an aryloxy radical, an aryl radical, a nitro function, a polyether radical, an aryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl radical having from 1 to 12 carbon atoms.

20. The polycyclic compound as defined by claim 1, selected from the group consisting of:

1. 2-[3'-({[6-(2-Methoxyethoxymethoxy)naphthalene-2-carbonyl]methylamino}methyl)biphenyl-4-ylamino] methyl benzoate;
2. 2-[3'-({[6-(2-Methoxyethoxymethoxy)naphthalene-2-carbonyl]methylamino}methyl)biphenyl-4-ylamino] benzoic acid;
3. N-{4'-[2-(2,5-Difluorobenzylcarbamoyl)phenylamino] biphenyl-3-ylmethyl}-N-methyl-6-(2-methoxy-ethoxymethoxy)naphthalene-2-carboxylamide;
4. N-{4'-[2(Benzylmethylcarbamoy)phenylamino]biphenyl-3-ylmethyl}-N-methyl-6-(2-methoxy-ethoxymethoxy)naphthalene-2-carboxylamide;
5. 2-{3'-[(Methyloctanoylamino)methyl]biphenyl-4-ylamino}methyl benzoate;
6. 2-{3'-[(Methyloctanoylamino)methyl]biphenyl-4-ylamino}benzoic acid;
7. 2-(Methyl{3'-[(methyloctanoylamino)methyl]biphenyl-4-yl}amino)methyl benzoate;
8. 2-(Methyl-{3'-[(methyloctanoylamino)-methyl]biphenyl-4-yl}amino)benzoic acid;
9. N-(3-Methylbutyl)-2-{3'-[(methyloctanoylamino)methyl]biphenyl-4-ylamino}benzamide;
10. N-Methyl-N-{4'-[2-(5-propyl-[1,3,4]oxadiazol-2-yl)-phenylamino]biphenyl-3-ylmethyl}octanoylamide;
11. N-Methyl-N-{4'-[2-(1H-tetrazol-5-yl)phenylamino] biphenyl-3-ylmethyl}octanoylamide;
12. 3-[3'({(6-(2-Methoxyethoxymethoxy)naphthalene-2-carbonyl]methylamino}methyl)biphenyl-4-ylamino] ethyl benzoate;
13. 3-[3'-({[6-(2-Methoxyethoxymethoxy)naphthalene-2-carbonyl]methylamino}methyl)biphenyl-4-ylamino] benzoic acid;
14. 3-(3'-{[(6-Hydroxynaphthalene-2-carbonyl)methylamino]methyl}biphenyl-4-ylamino)ethyl benzoate;
15. 3-(3'-{[(6-Hydroxynaphthalene-2-carbonyl)methylamino]methyl}biphenyl-4-ylamino)benzoic acid;
16. N-Methyl-N-{4'-[3-(4-methylpiperidine-1-carbonyl)-phenylamino]biphenyl-3-ylmethyl}6-(2-methoxy-ethoxymethoxy)naphthalene-2-carboxylamide;
17. N-Methyl-N-{4'[3-(morpholine-4-carbonyl)-phenylamino]biphenyl-3-ylmethyl}-6-(2-methoxy-ethoxymethoxy)naphthalene-2-carboxylamide;
18. N-Methyl-N-{4'-[3-(4-methylpiperidine-1-carbonyl) phenylamino]bipheny-3-ylmethyl}-6-hydroxynaphthalene-2-carboxylamide;
19. N-Methyl-N-{4'[3-(morpholine-4-carbonyl)phenylamino]biphenyl-3-ylmethyl}-6-hydroxynaphtalene-2-carboxylamide;
20. 3-{3'-[(Methyloctanoylamino)methyl]biphenyl-4-ylamino}benzoic acid;
21. 2-{3'-[(Methyloctanoylamino)methyl]biphenyl-4-yloxy}ethyl benzoate;
22. 2-{3'-[(Methyloctanoylamino)methyl]biphenyl-4-yloxy}benzoic acid;
23. 2-[3'-(1-Methyl-3-naphthalene-2-ylureido)biphenyl-4-ylamino]benzoic acid;
24. 2-{[3'-(3-Heptyl-1-methylureido)biphenyl-4-yl] methylamino}benzoic acid;
25. 2-(3'-{[Methyl(quinoxaline-6-carbonyl)amino] methyl}biphenyl-4-ylamino)benzoic acid;
26. 2-(3'-{[(2–1H-Benzoimidazol-2-ylacetyl)methylamino]methyl}biphenyl-4-ylamino)benzoic acid;
27. 2-[3'-(1-Methyl-3-thiophene-3-ylureido)biphenyl-4-ylamino]benzoic acid;
28. 2-[3'-(3-Benzo[1,2,5]thiadiazol-5-yl-1-methylureidobiphenyl-4-ylamino]benzoic acid;
29. 1-Methyl-1-{4'-[3-(morpholine-4-carbonyl)phenylamino]bipheny-3-yl}-3-naphth-2-yl-urea;
30. N-Methyl-3-[3'-(1-methyl-3-naphth-2-ylureido)biphenyl-4-ylamino]-N-phenethylbenzamide;
31. 3-{Methyl-[3'-(1-methyl-3-naphth-2-ylureido)biphenyl-4-yl]amino}benzoic acid;
32. 3-(3'-{[Methyl(quinoxaline-6-carbonyl)-amino] methyl}biphenyl-4-ylamino)isobutyl benzoate;
33. 3-[3'-({[6-(2-Methoxyethoxymethoxy)naphthalene-2-carbonyl]methylamino}methyl)biphenyl-4-ylmethyl] benzoic acid;
34. 2-{3'[3-(4-Dimethylaminophenyl)-1-methylureido] biphenyl-4-ylsulfanyl}benzoic acid;
35. 2-[3'-(3-Benzo[1,2,5]thiadiazol-5-yl-1-methylureido) biphenyl-4-yloxy]benzoic acid;
36. 2-Morpholin-4-ylethyl 3-(3'-{[methyl(quinoxaline-6-carbonyl)amino]methyl}biphenyl-4-yloxy)benzoate;
37. N-{4'[3-(2-Dimethylaminoethylcarbamoyl)phenoxy] biphenyl-3-ylmethyl}-N-methyl-6-(2-methoxyethoxy) naphthalene-2-carboxylamide;
38. 3-[3'-({[6-(2-Methoxyethoxymethoxy)naphthalene-2-carbonyl]amino}methyl)biphenyl-4-ylamino]benzoic acid;
39. 3-{3'-[6-(2-Methoxyethoxymethoxy)naphth-2-yloxycarbonylmethyl]biphenyl-4-ylamino}benzoic acid;
40. 2-[3'-(3-Heptyl-1-methylureido)biphenyl-4-ylamino] benzoic acid;
41. 3-Heptyl-1-methyl-1-{4'-[2-(morpholine-4-carbonyl) phenylamino]biphenyl-3-yl}-urea;
42. 3-Heptyl-1-methyl-1-(4'-{methyl-[2-(morpholine-4-carbonyl)phenyl]amino}biphenyl-3-yl)urea;
43. 3-Heptyl-1-methyl-1-(4'-{methyl-[2-(4-methylpiperidine-1-carbonyl)phenyl]amino}biphenyl-3-yl)urea;
44. 3-Heptyl-1-methyl-1-{4'-[2-(4-methylpiperidine-1-carbonyl)phenylamino]biphenyl-3-yl}urea;
45. 2-[3'-(3-Heptyl-1-methylureido)biphenyl-4-ylsulfanyl]benzoic acid;
46. 2-[3'-(3-Heptyl-1-methylureido)biphenyl-4-ylmethyl] benzoic acid;
47. 2-[3'-(1-Methyl-3-pentylureido)biphenyl-4-ylamino] benzoic acid;
48. 1-Methyl-1-{4'-[2-(morpholine-4-carbonyl)phenylamino]biphenyl-3-yl}-3-pentylurea;
49. 2-[3'-(3-Heptyl-1-methylthioureido)biphenyl-4-ylamino]benzoic acid;
50. 3-Hepty-1-methyl-1-{4'-[2-(5-propyl-[1,3,4]oxadiazol-2-yl)phenylamino]biphenyl-3-yl}urea;
51. 3-Heptyl-1-methyl-1-{4'-[2-(1H-tetrazol-5-yl)phenylamino]biphenyl-3-yl}urea;
52. 2-{3'-[(Hexanoylmethylamino)methyl]biphenyl-4-ylamino}benzoic acid;
53. N-Methyl-N-{4'-[2-(morpholine-4-carbonyl)phenylamino]biphenyl-3-ylmethyl}hexanoylamide;
54. 2-(3'-{[Methyl-(5-oxohexanoy)amino] methyl}biphenyl-4-ylamino)benzoic acid;
55. 2-(3'-{[Methyl-(4-methylaminobutyryl)amino] methyl}biphenyl-4-ylamino)benzoic acid;

56. 2-[3'-({[3-(N',N'-Dimethyl-hydrazinocarbonyl)propionyl]methylamino}methyl)-biphenyl-4-ylamino]benzoic acid;
57. 2-[3'(3-Heptyl-1-methylureido)biphenyl-4-ylamino]-N-hydroxybenzamide;
58. 2-[3-Fluoro-3'-(3-heptyl-1-methylureido)biphenyl-4-ylamino]benzoic acid;
59. 2-[3-Fluoro-3'-(1-methyl-3-pentylureido)biphenyl-4-ylamino]benzoic acid;
60. 2-[2-Fluoro-3'-(1-methyl-3-pentylureido)biphenyl-4-ylamino]benzoic acid;
61. 2-[2-Fluoro-3'-(3-heptyl-1-methylureido)biphenyl-4-ylamino]benzoic acid;
62. N-Methyl-N-{4'-[3-(2-piperidin-1-ylethylcarbamoyl)phenylamino]biphenyl-3-ylmethyl}-6-(2-methoxyethoxymethoxy)naphthalene-2-carboxylamide;
63. N-Methyl-N-{4'-[3-(2-morpholin-4-ylethylcarbamoyl)-phenylamino]biphenyl-3-ylmethyl}-6-(2-methoxyethoxymethoxy)naphthalene-2-carboxylic acid amide;
64. N-Methyl-N-{4'-[2-(morpholine-4-carbonyl)phenylamino]biphenyl-3-ylmethyl}-6-(2-methoxyethoxymethoxy)naphthalene-2-carboxylic acid amide;
65. N-Methyl-N-{4'-[2-(4-methylpiperidine-1-carbonyl)phenylamino]biphenyl-3-ylmethyl}-6-(2-methoxyethoxymethoxy)naphthalene-2-carboxylamide;
66. 2-(3'-{[(6-Hydroxynaphthalene-2-carbonyl)methylamino]methyl}biphenyl-4-ylamino)benzoic acid;
67. 2-[3'-(3-Hexyl-1-methylthioureido)biphenyl-4-ylamino]benzoic acid;
68. 2-{3'-[(Methyloctanethioylamino)methyl]biphenyl-4-ylamino}benzoic acid;
69. 2-{4'-Fluoro-3'-[(methyloctanoylamino)methyl]biphenyl-4-ylamino}benzoic acid;
70. 2-{2'-Fluoro-5'-[(methyloctanoylamino)methyl]biphenyl-4-ylamino}benzoic acid;
71. 3-Heptyl-1-methyl-1-{4'-[2-(pyrazole-1-carbonyl)phenylamino]biphenyl-3-yl}urea;
72. 2-(3'-{[Methyl-(1,4,5,6-tetrahydrocyclopentapyrazole-3-carbonyl)amino]methyl}biphenyl-4-ylamino)benzoic acid;
73. 2-(3'-{[Methyl-(2-methylthiazolidine-4-carbonyl)methyl}biphenyl-4-ylamino)benzoic acid;
74. 2-[3'-({[Methyl-[2-(3-methylbenzoylamino)acetyl]amino}methyl)biphenyl-4-ylamino]benzoic acid;
75. 2-(3'-{[Methyl-(3-phenylpropionyl)amino]methyl}biphenyl-4-ylamino)benzoic acid;
76. 2-{3'-[(Methyloctanoylamino)methyl]biphenyl-4-ylamino}-N-(2-morpholin-4-ylethyl)benzamide;
77. 2-(3'-{[(9H-Fluoren-9-ylmethoxycarbonyl)methylamino]methyl}biphenyl-4-ylamino)benzoic acid;
78. N-Methyl-N-{4'-[2-(4-methylimidazole-1-carbonyl)phenylamino]biphenyl-3-ylmethyl}octanoylcarboxylamide;
79. 1-[4'-(2-Benzoylphenylamino)biphenyl-3-yl]-3-heptyl-1-methylurea;
80. 2-[3'-(3-Heptyl-1-methylureido)biphenyl-4-ylamino]-N-methyl-N-piperidin-1-ylbenzamide;
81. 2-[3'-(3-Heptyl-1-methylureido)biphenyl-4-ylamino]-N-methyl-N-phenyl-benzamide; and mixtures thereof.

21. The polycyclic compound as defined by claim 1, having at least one of the following characteristics:

$R_1$ is a radical of formula (b), in which $R_5$ is a hydroxyl group, a heterocyclic radical or NR'R'';

A is a linking radical of structure —$CH_2N(R_{10})$—CO or —$N(R_{10})$—CO-(D) wherein r=0 or 1;

$R_3$ is an alkyl, aryl or heteroaryl radical;

X is an oxygen atom or a radical $NR_9$ in which $R_9$ is a hydrogen atom or an alkyl radical having from 1 to 4 carbon atoms.

22. A pharmaceutical composition useful for modulating the properties of PPAR receptors, or for regulating and/or restoring the metabolism of skin lipids, comprising a thus effective amount of the polycyclic compound as defined by claim 1, formulated into a physiologically acceptable support therefor.

23. A cosmetic composition useful for body and/or hair hygiene, comprising a thus effective amount of the polycyclic compound as defined by claim 1, formulated into a cosmetically acceptable support therefor.

* * * * *